US006156923A

United States Patent [19]
Farooq et al.

[11] Patent Number: 6,156,923
[45] Date of Patent: Dec. 5, 2000

[54] PROCESS FOR THE PREPARATION OF PESTICIDES

[75] Inventors: Saleem Farooq, Arisdorf, Switzerland; Stephan Trah, Freiburg, Germany; Hugo Ziegler, Witterswil; René Zurflüh, Basel, both of Switzerland

[73] Assignee: Novartis Corporation, Summit, N.J.

[21] Appl. No.: 08/762,217

[22] Filed: Dec. 6, 1996

[30] Foreign Application Priority Data

Dec. 7, 1995 [CH] Switzerland ............ 3464/95

[51] Int. Cl.$^7$ ............ C07C 249/04; C07C 249/12
[52] U.S. Cl. ............ 560/35; 556/419; 558/391; 564/164; 564/165
[58] Field of Search ............ 560/35; 564/164, 564/165, 156; 556/419; 558/391

[56] References Cited

U.S. PATENT DOCUMENTS

| | | | |
|---|---|---|---|
| 5,346,902 | 9/1994 | Clough et al. | 514/269 |
| 5,371,084 | 12/1994 | de Fraine et al. | 514/241 |
| 5,387,607 | 2/1995 | Brand et al. | 514/513 |
| 5,563,168 | 10/1996 | Brand et al. | 514/357 |

FOREIGN PATENT DOCUMENTS

| | | |
|---|---|---|
| 9178167 | 12/1991 | Australia . |
| 9526710 | 5/1996 | Australia . |
| 0370629 | 5/1990 | European Pat. Off. . |
| 0414153 | 2/1991 | European Pat. Off. . |
| 0460575 | 12/1991 | European Pat. Off. . |
| 0463488 | 1/1992 | European Pat. Off. . |
| 0472300 | 2/1992 | European Pat. Off. . |
| 0506149 | 9/1992 | European Pat. Off. . |
| 0617014 | 9/1994 | European Pat. Off. . |
| 9007493 | 7/1990 | WIPO . |
| 9213830 | 8/1992 | WIPO . |
| 9218487 | 10/1992 | WIPO . |
| 9218494 | 10/1992 | WIPO . |
| 9518789 | 7/1995 | WIPO . |
| 9521153 | 8/1995 | WIPO . |
| 9521154 | 8/1995 | WIPO . |
| 9521156 | 8/1995 | WIPO . |
| 9534526 | 12/1995 | WIPO . |
| 9611183 | 4/1996 | WIPO . |
| 9616026 | 5/1996 | WIPO . |
| 9632373 | 10/1996 | WIPO . |
| 9635669 | 11/1996 | WIPO . |

OTHER PUBLICATIONS

Derwent Abstract 97–011705 (1997).
Derwent Abstract 95–292864 (1995).
Derwent Abstract 95–292863 (1995).
Derwent Abstract 95–292862 (1995).
Derwent Abstract 96–477039 (1996).

*Primary Examiner*—Peter O'Sullivan
*Attorney, Agent, or Firm*—William A. Teoli, Jr.

[57] ABSTRACT

The invention relates to a process for the preparation of compounds of the formula (I)

[chemical structure]

or, if appropriate, a tautomer thereof, in each case in the free form or in salt form, in which A, X, Y, Z, $R_2$, $R_3$, $R_4$, $R_5$, $R_7$, $R_9$ and n are as defined in claim 1 and the C═N double bond marked with E has the E configuration, which comprises a1) reacting either a compound of the formula (II) mentioned above with a compound of the formula (III) mentioned above, in which $X_1$ is a leaving group, or a2) a compound of the formula (IV) mentioned above, if appropriate in the presence of a base, with a compound of the formula (V) mentioned above, or b1) reacting a compound of the formula (VI) mentioned above with a compound of the formula $R_7$—A—$X_2$ (VII), in which $X_2$ is a leaving group, and either further reacting the compound thus obtainable, of the formula (IV), for example according to method a2), or b2) reacting it with hydroxylamine or a salt thereof, if appropriate in the presence of a basic or acid catalyst, and further reacting the compound thus obtainable, of the formula (II), for example according to method a1), or c) reacting a compound of the formula (VII), mentioned above with a $C_1$–$C_6$alkyl nitrite and further reacting the compound thus obtainable, of the formula (VI), for example according to method b), the E isomers of the compounds of the formulae (II), (IV) and (VI), a process for their preparation and their use for the preparation of compounds of the formula (I).

17 Claims, No Drawings

PROCESS FOR THE PREPARATION OF PESTICIDES

The invention relates to a process for the preparation of compounds of the formula

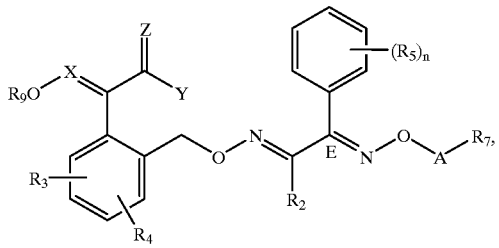

(I)

and, where appropriate, their tautomers, in each case in the free form or salt form, in which either X is CH or N, Y is $OR_1$ and Z is O, or
X is N, Y is $NHR_8$ and Z is O, S or S(=O);
$R_1$ is $C_1$–$C_4$alkyl;
$R_2$ is H, $C_1$–$C_4$alkyl, halogeno-$C_1$–$C_4$alkyl, $C_3$–$C_6$cycloalkyl or $C_1$–$C_4$alkoxymethyl;
$R_3$ and $R_4$ independently of one another are H, $C_1$–$C_4$alkyl, $C_1$–$C_4$alkoxy, OH, CN, $NO_2$, a $(C_1$–$C_4$alkyl$)_3$—Si group, where the alkyl groups can be identical or different, halogen, $(C_1$–$C_4$alkyl$)$S(=O)$_m$, (halogeno-$C_1$–$C_4$alkyl)S(=O)$_m$, halogeno-$C_1$–$C_4$alkyl or halogeno-$C_1$–$C_4$alkoxy;
$R_5$ is $C_1$–$C_6$alkyl, halogeno-$C_1$–$C_6$alkyl, $C_1$–$C_6$alkoxy, halogeno-$C_1$–$C_6$alkoxy, $C_1$–$C_6$-alkylthio, halogen-$C_1$–$C_6$alkylthio, $C_1$–$C_6$alkylsulfinyl, halogeno-$C_1$–$C_6$-alkylsulfinyl, $C_1$–$C_6$alkylsulfonyl, halogeno-$C_1$–$C_6$alkylsulfonyl, $C_1$–$C_6$alkoxy-$C_1$–$C_6$alkyl, halogeno-$C_1$–$C_6$alkoxy $C_1$–$C_6$alkyl, $C_1$–$C_6$alkylthio-$C_1$–$C_6$alkyl, halogeno-$C_1$–$C_6$alkylthio-$C_1$–$C_6$alkyl, $C_1$–$C_6$alkylsulfinyl-$C_1$–$C_6$alkyl, halogeno-$C_1$–$C_6$-alkylsulfinyl-$C_1$–$C_6$alkyl, $C_1$–$C_6$-alkylsulfonyl-$C_1$–$C_6$alkyl, halogeno-$C_1$–$C_6$-alkylsulfonyl-$C_1$–$C_6$alkyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylaminocarbonyl, $C_1$–$C_4$-alkoxyiminomethyl; di($C_1$–$C_6$alkyl)-aminocarbonyl, where the alkyl groups can be identical or different; $C_1$–$C_6$-alkylaminothiocarbonyl; di($C_1$–$C_6$alkyl)-aminothiocarbonyl, where the alkyl groups can be identical or different; $C_1$–$C_6$-alkylamino, di($C_1$–$C_6$alkyl)-amino, where the alkyl groups can be identical or different; halogen, $NO_2$, CN, $SF_5$, thioamido, thiocyanatomethyl; an unsubstituted or mono- to tetrasubstituted $C_1$–$C_4$alkylenedioxy group, where the substituents are selected from the group consisting of $C_1$–$C_4$alkyl and halogen; or $QR_6$, where, if n is greater than 1, the radicals $R_5$ can be identical or different;
$R_6$ is $C_2$–$C_6$alkenyl or $C_2$–$C_6$ alkynyl which are unsubstituted or substituted by 1 to 3 halogen atoms; $(C_1$–$C_4$alkyl$)_3$Si, where the alkyl groups can be identical or different; CN; or an unsubstituted or mono- to pentasubstituted $C_3$–$C_6$cycloalkyl, aryl or heterocyclyl group, where the substituents are selected from the group consisting of halogen, $C_1$–$C_6$alkyl, halogeno-$C_1$–$C_6$alkyl, $C_1$–$C_6$alkoxy, halogeno-$C_1$–$C_6$alkoxy, phenoxy, naphthoxy and CN;
A either is a direct bond, $C_1$–$C_{10}$alkylene, —C(=O)—,—C(=S)— or halogeno-$C_1$–$C_{10}$alkylene and $R_7$ is a radical $R_{10}$, or is $C_1$–$C_{10}$alkylene, —C(=O)—,—C(=S)— or halogeno-$C_1$–$C_{10}$alkylene and $R_7$ is $OR_{10}$, $N(R_{10})_2$, where the radicals $R_{10}$ can be identical or different, or —S(=O)$_q$$R_{10}$;
$R_8$ is H or $C_1$–$C_4$alkyl;
$R_9$ is methyl, fluoromethyl or difluoromethyl;
$R_{10}$ is H; an unsubstituted or substituted $C_1$–$C_6$alkyl, $C_2$–$C_6$alkenyl or $C_2$–$C_6$alkynyl group, where the substituents are selected from the group consisting of halogen; $(C_1$–$C_4$alkyl$)_3$Si, where the alkyl groups can be identical or different; $C_3$–$C_6$cyclo-alkyl, which is unsubstituted or substituted by halogen; $C_1$–$C_6$alkoxycarbonyl, which is unsubstituted or substituted by halogen; unsubstituted or substituted aryl, where the substituents are selected from the group consisting of halogen, halogeno-$C_1$–$C_4$alkyl and CN; a $(C_1$–$C_4$alkyl$)_3$Si group, where the alkyl groups can be identical or different; $C_3$–$C_6$cycloalkyl, which is unsubstituted or substituted by halogen; $C_1$–$C_6$alkoxycarbonyl which is unsubstituted or substituted by halogen; or an unsubstituted or substituted aryl or heterocyclyl group, where the substituents are selected from the group consisting of halogen and halogeno-$C_1$–$C_4$alkyl;
Q is a direct bond, $C_1$–$C_8$alkylene, $C_2$–$C_6$alkenylene, $C_2$–$C_6$alkynylene, O, O($C_1$–$C_6$alkylene), ($C_1$–$C_6$alkylene)O, S(=O)$_p$, S(=O)$_p$($C_1$–$C_6$alkylene) or ($C_1$–$C_6$alkylene)S(=O)$_p$;
m is 0, 1 or 2;
n is 0, 1, 2, 3, 4 or 5;
p is 0, 1 or 2; and
q is 0, 1 or 2,
and the C=N double bond marked with E has the E configuration,
which comprises
a1) reacting either a compound of the formula

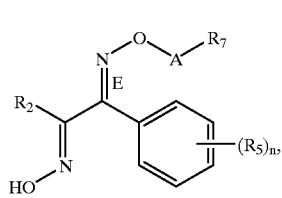

(II)

in which A, $R_2$, $R_5$, $R_7$ and n are as defined for formula I and the C=N double bond marked with E has the E configuration, or a tautomer thereof, in each case in the free form or in salt form, if appropriate in the presence of a base, with a compound of the formula

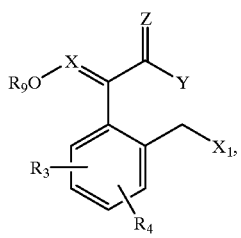
(III)

which is known or can be prepared by methods known per se and in which X, Y, Z, $R_3$, $R_4$ and $R_9$ are as defined for formula I and $X_1$ is a leaving group, or a tautomer thereof, in each case in the free from or in salt form, or a2) reacting a compound of the formula

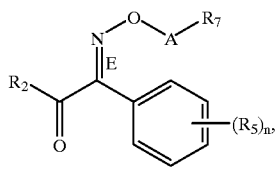
(IV)

in which A, $R_2$, $R_5$, $R_7$ and n are as defined for formula I and the C=N double bond marked with E has the E configuration, or a tautomer thereof, in each case in the free form or in the salt form, if appropriate in the presence of a base, with a compound of the formula

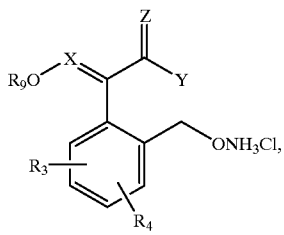
(V)

which is known or can be prepared by methods known per se and
in which X, Y, Z, $R_3$, $R_4$ and $R_9$ are as defined for formula I, or a tautomer thereof, in each case in the free form or in salt form, or b1) reacting a compound of the formula

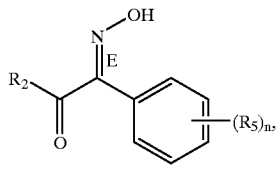
(VI)

in which $R_2$, $R_5$ and n are as defined for formula I and the C=N double bond marked with E has the E configuration, or a tautomer thereof, in each case in the free form or in salt form, if appropriate in the presence of a base, with a compound of the formula

$R_7$—A—$X_2$ (VII), which is known or can be prepared by methods known per se and in which A and $R_7$ are as defined for formula I and $X_2$ is a leaving group, and either further reacting the compound thus obtainable, of the formula IV, for example according to method a2), or b2) reacting it with hydroxylamine or a salt thereof, if appropriate in the presence of a base or acid catalyst, and further reacting the compound thus obtainable, of the formula II, for example according to method a1), or c) reacting a compound of the formula

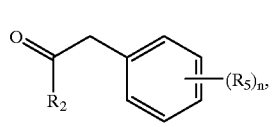
(VIII)

which is known or can be prepared by methods known per se and
in which $R_2$, $R_5$ and n are as defined for formula I, or a tautomer thereof, in each case in the free form or in salt form, if appropriate in the presence of a base, with a $C_1$–$C_6$alkyl nitrite, and further reacting the compound thus obtainable, of the formula VI, for example according to method b), the E isomers of the compounds of the formulae II, IV and VI, or a tautomer thereof, in each case in the free form or in salt form, a process for their preparation and their use for the preparation of compounds of the formula I.

The compounds of the formula I are known pesticides. The processes known to date for their preparation give mixtures of E and Z isomers in respect of the C=N double bond marked with E in formula I of different composition, depending on the process. Since the biological properties of the E isomers are in each case found to be superior to those of the mixtures and of the Z isomers, there is a need to develop preparation processes for compounds of the formula I having the isomerically pure E configuration. This object is achieved by the preparation process according to the invention.

Unless defined differently, the general terms used above and below are defined as follows.

Carbon-containing groups and compounds in each case contain 1 up to and including 8, preferably 1 up to and including 6, in particular 1 up to and including 4, especially 1 or 2, carbon atoms.

Alkyl—as a group per se and as a structural element of other groups and compounds, such as of halogenoalkyl, alkoxy, alkylthio, alkylsulfinyl, alkylsulfonyl, alkylcarbonyl, alkoxycarbonyl, halogenoalkoxycarbonyl, alkylaminocarbonyl, alkoxyiminomethyl, alkylaminothiocarbonyl and alkylamino—is, in each case taking into due consideration the number, included from case to case, of carbon atoms contained in the corresponding group or compound, either straight-chain, i.e. methyl, ethyl, propyl, butyl, pentyl or hexyl, or branched, for example isopropyl, isobutyl, sec-butyl, tert-butyl, isopentyl, neopentyl or isohexyl.

Alkenyl—as a group per se and as a structural element of other groups and compounds, such as of halogenoalkenyl—is, in each case under due consideration of the number, included from case to case, of carbon atoms contained in the corresponding group or compound, either straight-chain, for example vinyl, 1-methylvinyl, allyl, 1-butenyl or 2-hexenyl, or branched, for example iso-propenyl.

Alkynyl—as a group per se and as a structural element of other groups and compounds, such as of halogenoalkynyl—is, in each case under due consideration of the number, included from case to case, of carbon atoms contained in the corresponding group or compound, either straight-chain, for example propargyl, 2-butynyl or 5-hexynyl, or branched, for example 2-ethynylpropyl or 2-propargylisopropyl.

$C_3$–$C_6$cycloalkyl is cyclopropyl, cyclobutyl, cyclopentyl or cyclohexyl.

Alkylene—as a group per se and as a structural element of other groups and compounds, such as of O(alkylene), (alkylene)O, $S(=O)_p$(alkylene), (alkylene)$S(=O)_p$ or alkylenedioxy—is, in each case under due consideration of the number, included from case to case, of carbon atoms contained in the corresponding group or compound, either straight-chain, for example —$CH_2CH_2$—, —$CH_2CH_2CH_2$— or —$CH_2CH_2CH_2CH_2$—, or branched, for example —$CH(CH_3)$—, —$CH(C_2H_5)$—, —$C(CH_3)_2$—, —$CH(CH_3)CH_2$— or —$CH(CH_3)CH(CH_3)$—.

Alkenylene is, in each case under due consideration of the number, from case to case, of carbon atoms contained in the corresponding compound, either straight-chain, for example vin-1,2-ylene, all-1,3-ylene, but-1-en-1,4-ylene or hex-2-en-1,6-ylene, or branched, for example 1-methylvin-1,2-ylene.

Alkynylene is, in each case under due consideration of the number, from case to case, of carbon atoms contained in the corresponding compound, either straight-chain, for example propargylene, 2-butynylene or 5-hexynylene, or branched, for example 2-ethynylpropylene or 2-propargylisopropylene.

Aryl is phenyl or naphthyl, in particular phenyl.

Heterocyclyl is a 5- to 7-membered aromatic or non-aromatic ring having one to three heteroatoms, which are selected from the group consisting of N, O and S. 5- and 6-membered rings which contain a nitrogen atom as a heteroatom and, if appropriate, a further heteroatom, preferably nitrogen or sulfur, in particular nitrogen, are preferred.

Halogen—as a group per se and as a structural element of other groups and compounds, such as of halogenoalkyl, halogenoalkenyl and halogenoalkynyl—is fluorine, chlorine, bromine or iodine, especially fluorine, chlorine or bromine, in particular fluorine or chlorine, very especially fluorine.

Halogen-substituted carbon-containing groups and compounds, such as halogenoalkyl, halogenoalkenyl or halogenoalkynyl, can be partly halogenated or perhalogenated, and in the case of polyhalogenation, the halogen substituents can be identical or different. Examples of halogenoalkyl—as a group per se and as a structural element of other groups and compounds, such as of halogenoalkenyl—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers which is mono- to nonasubstituted by fluorine, chlorine and/or bromine, such as $CF(CF_3)$—$CHFCF_3$ or $CH_2(CF_2)_2CF_3$. Halogenoalkenyl is, for example, $CH_2CH=CHCl$, $CH_2CH=CCl_2$, $CH_2CF=CF_2$ or $CH_2CH=CHCH_2Br$. Halogenoalkynyl is, for example, $CH_2C\equiv CF$, $CH_2C\equiv CCH_2Cl$ or $CF_2CF_2C\equiv CCH_2F$.

Some compounds I to VI and VIII can be present as tautomers, as is familiar to the expert, in particular if $AR_7$ is H. Compounds I above and below are therefore also to be understood as meaning corresponding tautomers, even if the latter are not mentioned specifically in each case.

Compounds I to VI and VIII which contain at least one basic centre, can form, for example, acid addition salts. These are formed, for example, with strong inorganic acids, such as mineral acids, for example perchloric acid, sulfuric acid, nitric acid, nitrous acid, a phosphoric acid, or a hydrogen halide acid, with strong inorganic carboxylic acids, such as $C_1$–$C_4$alkanecarboxylic acids which are unsubstituted or substituted, for example by halogen, for example acetic acid, such as dicarboxylic acids which are saturated or unsaturated, for example oxalic, malonic, succinic, maleic, fumaric or phthalic acid, such as hydroxycarboxylic acids, for example ascorbic, lactic, malic, tartaric or citric acid, or such as benzoic acid, or with organic sulfonic acids, such as $C_1$–$C_4$alkane- or arylsulfonic acids which are unsubstituted or substituted, for example by halogen, for example methane- or p-toluenesulfonic acid. Compounds I with at least one acid group can furthermore form salts with bases. Suitable salts with bases are, for example, metal salts such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono-, di- or trihydroxy-lower alkylamine, for example mono-, di- or triethanolamine. Furthermore, where appropriate, corresponding inner salts can be formed. Agrochemically advantageous salts are preferred in the context of the invention; however, salts which have disadvantages for agrochemical uses, for example salts which are toxic to bees or fish, which are employed, for example, for isolation or purification of free compounds I or agrochemically usable salts thereof, are also included. Compounds of the formulae I to VI and VIII in the free form and in the form of their salts are also to be understood above and below as meaning the corresponding salts or the free compounds I to VI and VIII. The same applies to tautomers of compounds of the formulae I to VI and VIII and salts thereof. In general, the free form is in each case preferred.

The reactions described above and below are carried out in a manner known per se, for example in the absence or usually in the presence of a suitable solvent or diluent or a mixture thereof, the reaction being carried out, as required, with cooling, at room temperature or with heating, for example in a temperature range from about −80° C. up to the boiling point of the reaction medium, preferably from about 0° C. up to about 150° C., and, if necessary, in a closed vessel, under pressure, in an inert gas atmosphere and/or under anhydrous conditions. Particularly advantageous reaction conditions can be seen from the examples.

The starting materials mentioned above and below, which are used for the preparation of the compounds I, in each case in the free form or in salt form, are known or can be prepared by methods known per se, for example in accordance with the following statements.

Variants a1/a2)

Suitable leaving groups $X_1$ in compounds III are, for example, hydroxyl, $C_1$–$C_8$alkoxy, halogeno-$C_1$–$C_8$alkoxy, $C_1$–$C_8$alkanoyloxy, mercapto, $C_1$–$C_8$alkylthio, halogeno-$C_1$–$C_8$alkylthio, $C_1$–$C_8$alkanesulfonyloxy, halogeno-$C_1$–$C_8$alkanesulfonyloxy, benzenesulfonyloxy, toluenesulfonyloxy and halogen, preferably toluenesulfonyloxy, trifluoromethanesulfonyloxy and halogen, in particular halogen.

Suitable bases for facilitating the reaction are, for example, alkali metal or alkaline earth metal hydroxides, hydrides, amides, alkanolates, acetates, carbonates, dialkylamides or alkylsilylamides, alkylamines, alkylenediamines, N-alkylated or non-alkylated, saturated or unsaturated cycloalkylamines, basic heterocyclic compounds, ammonium hydroxides and carbocyclic amines. Examples are sodium hydroxide, hydride, amide, methanolate, acetate and carbonate, potassium tert-butanolate, hydroxide, carbonate, and hydride, lithium diisopropylamide, potassium bis(trimethylsilyl)amide, calcium hydride, triethylamine, diisopropyl-ethyl-amine, triethylenediamine, cyclohexylamine, N-cyclohexyl-N,N-dimethyl-amine, N,N-diethylaniline, pyridine, 4-(N,N-dimethylamino)pyridine, quinuclidine, N-methylmorpholine, benzyl-trimethyl-ammonium hydroxide and 1,5-diazabicyclo[5.4.0]undec-5-ene (DBU).

The reaction partners can be reacted with one another as such, i.e. without addition of a solvent or diluent, for example in the melt. However, the addition of an inert solvent or diluent or of a mixture thereof is usually advantageous. Examples of such solvents or diluents are: aromatic, aliphatic and alicyclic hydrocarbons and halogenohydrocarbons, such as benzene, toluene, xylene, mesitylene, tetralin, chlorobenzene, dichlorobenzene, bromobenzene, petroleum ether, hexane, cyclohexane, methylene chloride, chloroform, carbon tetrachloride, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitriles such as acetonitrile or propionitrile; and sulfoxides, such as dimethyl sulfoxide. If the reaction is carried out in the presence of a base, bases employed in excess, such as triethylamine, pyridine, N-methylmorpholine or N,N-diethylaniline, can also serve as the solvent or diluent.

The reaction is advantageously carried out in a temperature range from about 0° C. up to about 180° C., preferably from about 10° C. up to about 80° C., in many cases in the range between room temperature and the reflux temperature of the reaction mixture.

The reaction is preferably carried out under normal pressure.

The reaction can be carried out without an inert gas atmosphere; preferably, however, it is carried out under an inert gas atmosphere, for example nitrogen or argon, in particular nitrogen.

The reaction time is not critical; a reaction time of about 0.1 to about 24 hours, in particular about 0.5 to about 2 hours, is preferred.

The product is isolated by customary methods, for example by filtration, crystallization, distillation or chromatography or any suitable combination of these processes.

In a preferred embodiment of variants a1/a2), a compound II is reacted with a compound III at 0° C. to 80° C., preferably 10° C. to 30° C., in an inert solvent, preferably an amide, in particular N,N-dimethylformamide in the presence of a metal hydride, preferably sodium hydride.

Particularly preferred conditions for the reaction are described in Examples H 1d) and H 3f).

The compounds of the formula III are known or can be prepared analogously to known compounds.

The compounds I are known. However, their preparation according to the prior art has a large number of serious industrial, ecological, economic and other disadvantages.

Thus, in the preparation processes according to the prior art, as a rule E/Z isomer mixtures with respect to the C=N double bond marked with E in formula I are obtained. Since the biological properties of the E isomers are in each case found to be superior to those of the mixtures and of the Z isomers in each case, the processes according to the prior art have the significant disadvantage that products are produced which are either significantly less active as E/Z mixtures or from which the Z isomers must be removed in order to increase their biological activity, which means that many unnecessary handling operations must be carried out for separation of isomers, which has the effect of being very time-consuming, blocks valuable production lines for a long time and is associated with high additional energy costs. The removal of the less active Z isomer also leads to additional enormous losses in yield, which in turn not only is problematic and ecologically disadvantageous, but also renders the process according to the prior art much more expensive and consequently economically of no interest. The industrial, ecological, economic and other disadvantages of the processes according to the prior art are not limited to those described above, these latter being intended to serve only as a few examples of the large number of disadvantages of the processes according to the prior art. The disadvantages of the processes according to the prior art cause serious problems even when the processes are carried out on a laboratory scale. When the processes are carried out on a larger scale, these disadvantages intensify considerably. In the end, however, the aim is to carry out a specific process on an industrial scale if this process is to be suitable for preparing products for agrochemical purposes.

According to the process of the present invention, the compounds I are prepared by reaction of the compound II with a compound III or by reaction of the compound IV with a compound V. These processes according to the invention have extremely surprising industrial, ecological, economic and other advantages compared with the processes from the prior art. Since the compounds II or, respectively, IV are present in the preparation process according to the invention as pure E isomers in respect of the C=N double bond marked with E, only the E isomer of the compounds I is produced in the present process, which has the effect of an enormous saving in time and at the same time a high saving in cost and energy, since no valuable production lines are blocked for a long time for separation of the isomers, and at the same time the amount of biologically more active E isomer produced by per unit time is much higher than in the processes according to the prior art. The resources such as starting products and energy are consequently utilized to the optimum in the present process, which not only very greatly simplifies the process and renders it ecologically advantageous, but consequently renders it cheaper and therefore of greater economic interest. This means that all the disadvantages of the processes according to the prior art which can be attributed to the formation of E/Z isomers are avoided. The industrial, ecological, economic and other advantages of the process according to the invention are not limited only to those described above, these latter being intended to serve only as a few examples of the large number of advantages inherent in this process. Due to all the abovementioned advantages of the present process, the serious problems which occur in the processes according to the prior art are avoided even at the stage of a laboratory process. If the present process is used on a larger scale, these advantages prove to be even much more significant, which has the effect that these advantages first allow the process to be used on an industrial scale.

For this reason, all the industrial, ecological, economic and other disadvantages of the processes according to the prior art are surprisingly advantageously overcome in the preparation of compounds I by the present process.

Variant b)

The process according to variant b) is carried out by first reacting compound VI with compound VII, if appropriate further reacting the resulting product IV, if appropriate after isolation, with hydroxylamine or a salt thereof, and further reacting the resulting products II or, respectively, IV, if appropriate after isolation, in accordance with variants a1/a2), for example in the manner described above, to give the compounds I.

Suitable leaving groups $X_2$ in the compounds VII are, for example, those which are mentioned as examples for $X_1$ in variants a1/a2).

Suitable bases for facilitating the reaction are, for example, those which are mentioned in variants a1/a2).

The reaction partners can be reacted with one another as such, i.e. without addition of a solvent or diluent, for example in the melt. However, the addition of an inert solvent or diluent or of a mixture thereof is usually advantageous. Examples of such solvents or diluents are those mentioned in variants a1/a2).

The reaction is advantageously carried out in a temperature range from about 0° C. to about 180° C., preferably from about 10° C. to about 80° C., in many cases in the range between room temperature and the reflux temperature of the reaction mixture.

The reaction is preferably carried out under normal pressure.

The reaction can be carried out without an inert gas atmosphere; preferably, however, it is carried out under an inert gas atmosphere, for example nitrogen or argon, in particular nitrogen.

The reaction time is not critical; a reaction time of about 0.1 to about 24 hours, in particular about 0.5 to about 5 hours, is preferred.

The product is isolated by customary methods, for example filtration, crystallization, distillation or chromatography or any suitable combination of these processes.

In a preferred embodiment of variant b), a compound VI is reacted with a compound VII at 0° C. to 80° C., preferably 10° C. to 60° C., in an inert solvent, preferably a nitrile, in particular acetonitrile, in the presence of a metal carbonate, preferably potassium carbonate, and the compound IV thus obtainable is then further reacted, preferably in accordance with method a2).

Particularly preferred conditions for the reaction are described in Examples H 1b) to 1d) and H 3d) to 3f).

The compounds of the formula VII are known or can be prepared analogously to known compounds.

The present process according to the invention of variant b), which in principle is an advantageous combination of an O-alkylation reaction with process variants a1/a2) according to the invention, has all the great advantages compared with the prior art which have already been discussed above for the process according to the invention of variants a1/a2). In particular, the process of variant b) ensures that the E configuration of the C=N double bond marked with E in compound VI is retained. Furthermore, however, the process according to the invention of variant b) also has further industrial, ecological, economic and other advantages which are connected with the specific property that the intermediate product IV initially formed is not purified but is directly further processed as the moist crude product, in the case of intermediate isolation, or in situ in the reaction mixture, if it is not isolated. This missing purification step on the intermediate product mentioned is of advantage, for example, in as much as it is not necessary to dry it, which not only saves energy and further resources, but also enormously increases the safety of the preparation process, since the possible danger of a dust explosion of the dry intermediate product is averted completely. The savings in resources are even greater if the intermediate product is further reacted without purification, since, for example, no additional solvents are consumed for the recrystallization. The process of variant b) is of particular advantage compared with the individual process steps of the alkylation reaction of variants a1/a2) carried out in that the total reaction time in the process of variant b) is much shorter, which consequently leads to a much higher production of reaction product I per unit time and therefore to a much more efficient utilization of the valuable production lines. Furthermore, the total yield of reaction product I is surprisingly good when the process of variant b) is employed, and, compared with the combined yields of the individual process steps of the alkylation reaction and variants a1/a2) carried out, is in the same percentage range or even beffer. The industrial, ecological, economic and other advantages of the process according to the invention of variant b) are not limited to those described above, these latter being intended to serve only as a few examples of the large number of advantages inherent in the process according to the invention of variant b).

By using process variant b) according to the invention for preparation of the compounds I, a large number of industrial, ecological, economic and other advantages can therefore surprisingly be utilized efficiently.

Variant c)

The process according to variant c) is carried out by first reacting compound VIII with an alkylnitrite and further reacting the resulting product VI, if appropriate after isolation, in accordance with variant b), for example in the manner described above, to give the compounds I.

Suitable bases for facilitating the reaction are, for example, those which are mentioned in variants a1/a2).

The reaction partners can be reacted with one another as such, i.e. without addition of a solvent or diluent, for example in the melt. However, the addition of an inert solvent or diluent or of a mixture thereof is usually advantageous. Examples of such solvents or diluents are those mentioned in variants a1/a2).

The reaction is advantageously carried out in a temperature range from about 0° C. to about 180° C., preferably from about 0° C. to about 60° C., in many cases in the range between room temperature and the reflux temperature of the reaction mixture.

The reaction is preferably carried out under normal pressure.

The reaction can be carried out without an inert gas atmosphere; preferably, however, it is carried out under an inert gas atmosphere, for example nitrogen or argon, in particular nitrogen.

The reaction time is not critical; a reaction time of about 0.1 to about 24 hours, in particular about 0.5 to about 3 hours, is preferred.

The product is isolated by customary methods, for example filtration, crystallization, distillation or chromatography or any suitable combination of these processes.

In a preferred embodiment of variant c), a compound VIII is reacted with an alkyl nitrite at 0° C. to 80° C., preferably 0° C. to 40° C., in an inert solvent, preferably an alcohol, in particular methanol, in the presence of a metal alcoholate, preferably sodium methanolate, and the compound VI thus obtainable is then further reacted, preferably in accordance with method b).

Particularly preferred conditions for the reactions are described in Examples H 3d) to 3f).

The compounds of the formula VIII are known or can be prepared analogously to known compounds.

The present process according to the invention of variant c), which in principle is an advantageous combination of an oximation reaction with process variants a1/a2) and b) according to the invention, has all the great advantages compared with the prior art which have already been discussed above for the processes according to the invention of variants a1/a2) and b). Furthermore, the present oximation process for the preparation of the compounds VI surprisingly result exclusively in the E configuration of the C=N double bond marked with E in formula VI. It is thus ensured that the particular starting products II, IV or, respectively, VI in the subsequent processes according to the invention for the preparation of the compounds I, for example in process variants a1/a2) and b), are pure E isomers.

A large number of industrial, ecological, economic and other advantages can therefore surprisingly be utilized efficiently by using process variants c) according to the Invention for the preparation of the compounds of the formula I.

The E isomers of the compounds of the formulae II, IV and VI and tautomers thereof, in each case in the free form or in salt form, are novel and the present invention likewise relates to them.

The present invention furthermore relates to a process for the preparation of the E isomers of a compound of the formula VI or of a tautomer thereof, in each case in the free form or in salt form, according to the abovementioned process c), a process for the preparation of the E isomers of a compound of the formula IV, or of a tautomer thereof, in each case in the free form or in salt form, according to the abovementioned process b1), and a process for the preparation of the E isomers of a compound of the formula II, or of a tautomer thereof, in each case in the free form or in salt form, according to the abovementioned process b2).

The process conditions for the preparation of these intermediate products can be seen from the abovementioned processes a), b) and c).

PREPARATION EXAMPLE

Example H1

Methyl 2-[[[(1-methyl-2-phenyl-2-E-[(2-propynyl) oxyimino]-ethylidene)amino]oxy]methyl]α-(methoxymethylene)-phenylacetate (Compound 1.16)

H1a) 1-Phenyl-1,2-propanedione 1-E-oxime 69.7 g of a 30% solution of sodium methylate in methanol are added dropwise to a solution of 40.2 g of 1-phenyl-2-propanone and 36.1 g of isopentyl nitrite in 460 ml of methanol at 20–25°, while cooling. The reaction mixture is then further stirred at room temperature for 1 hour. After the solution has been concentrated in vacuo, the residue is dissolved in 600 ml of water, the solution is acidified with 10% hydrochloric acid, the product which precipitates out is filtered off and dissolved in ethyl acetate and the organic phase is washed twice with water, dried with sodium sulfate and evaporated in vacuo. The residue is stirred up in hexane and filtered. The title product is thus obtained with a melting of 168–70° C.

H1b) 1-Phenyl-1,2-propanedione 1-E-[(2-propynyl)oxime]

A mixture of 14 g of 1-phenyl-1,2-propanedione 1-E-oxime, 11.9 g of 1-bromo-2-propyne, 13.8 g of potassium carbonate and 0.5 g of potassium iodide in 170 ml of acetonitrile is stirred at 50° for 2 hours, the solvent is then distilled off in vacuo and the residue is dissolved again in ethyl acetate. The organic phase is washed in each case twice with water and saturated sodium chloride solution, dried with sodium sulfate and evaporated in vacuo. After recrystallization of the residue from hexane, 1-phenyl-1,2-propanedione 1-E-[(2-propynyl)oxime] is obtained with a melting point of 54–56° C.

H1d) 1-Phenyl-1,2-propanedione 1-E-[(2-propynyl)oxime]-2-oxime

A mixture of 14.3 g of 1-phenyl-1,2-propanedione 1-E-[(2-propynyl)oxime], 10.3 g of hydroxylamine hydrochloride and 11.7 g of pyridine in 230 ml of ethanol is boiled under reflux for 1 hour and then concentrated in vacuo, and 800 ml of water are added to the residue. The product which has precipitated out is filtered off and dissolved in ethyl acetate and the solution is washed three times with water, dried with sodium sulfate and evaporated in vacuo. The residue is suspended in hexane and filtered. The title product is thus obtained with a melting point of 163–165° C.

H1e) Methyl 2-[[[(1-methyl-2-phenyl-2-E-[(2-propynyl) oxyimino]ethy-lidene)amino]oxy]-methyl]-α-(methoxymethylene)-phenylacetate A solution of 5 g of 1-phenyl-1,2-propanedione 1-E-[(2-propynyl)oxime]-2-oxime in 24 ml of N,N-dimethylformamide is added dropwise to a suspension of 1.16 g of sodium hydride (about 55% in oil) in 45 ml of N,N-dimethylformamide at room temperature and the mixture is further stirred for 10 minutes. 6.5 g of methyl 2-(bromomethyl)-α-(methoxymethylene)-phenylacetate in 24 ml of N,N-dimethylformamide are then added dropwise and the reaction mixture is further stirred at room temperature for 1 hour. Thereafter, the mixture is acidified with acetic acid and evaporated in vacuo. The residue is dissolved in ethyl acetate and the solution is washed three times with water and twice with saturated sodium chloride solution, dried with sodium sulfate and evaporated in vacuo. After recrystallization of the residue from hexane/ethyl acetate, the title compound is obtained with a melting point of 82–84°.

Example H2

Methyl 2-[[[(1-methyl-2-(4-fluorophenyl)-2-E-[(2-propynyl)oxyimino]ethylidene)amino]oxy]methyl]-α-(methoxymethylene)-phenylacetate (compound 1.44)

The title compound with a melting point of 91–93° can be prepared in a manner analogous to that described in Example H1, starting from 1-(4-fluorophenyl)-2-propanone.

Example H3

Methyl 2-[[[(1-methyl-2-(4-(3-trifluoromethylphenylmethoxy)-phenyl) 2-E-[(2propynyl)oxyimino]ethylidene)amino]oxy] methyl]-α-(methoxymethylene)-phenylacetate (compound 1.240)

H3a) 1-(4-Hydroxyphenyl)-2-propanone

A mixture of 82 g of 1-(4-methoxyphenyl)-2-propanone, 500 ml of acetic acid and 500 ml of aqueous hydrobromic acid is boiled under reflux for 2 hours and then evaporated in vacuo. The oily residue is extracted four times with 700 ml of hexane/ether (5:2) each time, the extract is evaporated and the residue is chromatographed over silica gel using hexane/ethyl acetate (3:1). 1-(4-Hydroxyphenyl)-2-propanone is thus obtained with a melting point of 40–41°.

H3b) 1-[4-(3-Trifluoromethylphenylmethoxy)-phenyl]-2-propanone

A mixture of 5.8 g of 1-(4-hydroxyphenyl)-2-propanone, 61.6 g of potassium carbonate, 72.3 g of 1-(chloromethyl)-3-(trifluoromethyl)-benzene, and 1 g of potassium iodide in 800 ml of acetone is boiled under reflux for 5 hours. Thereafter, the reaction mixture is filtered and the filtrate is evaporated in vacuo. The residue is then dissolved in diethyl ether and the ethereal phase is washed three times with water, dried with sodium sulfate and evaporated. The 1-[4-(3-trifluoromethylphenylmethoxy)-phenyl]-2-propanone thus obtainable is employed in the next reaction stage without further purification.

H3c) 1-[4-(3-Trifluoromethylphenylmethoxy)-phenyl]-1,2-propanedione 1-E-oxime 45 g of a 30% solution of sodium methanolate in methanol are slowly added dropwise to a solution of 59.6 g of 1-[4-(3-trifluoromethylphenylmethoxy)-phenyl]-2-propanone and 23.4 g of isopentyl nitrite in 300 ml of methanol such that the temperature does not exceed 20–25°. The reaction mixture is then further stirred at room temperature for 1 hour and thereafter evaporated in vacuo. The residue is dissolved in 600 ml of water and the solution is acidified with 10% hydrochloric acid. The precipitate which separates out is filtered off and dissolved in ethyl acetate and the organic phase is washed twice with water, dried with sodium sulfate and evaporated. After the crude product has been suspended in hexane and filtered, 1-[4-(3-trifluoromethylphenylmethoxy)-phenyl]-1,2-propanedione 1-E-oxime is obtained with a melting point of 134–136°.

H3d) 1-[4-(3-Trifluoromethylphenylmethoxy)-phenyl]-1,2-propanedione 1-E-[(2-propynyl)oxime]

A mixture of 6 g of 1-[4-(3-trifluoromethylphenylmethoxy)-phenyl]-1,2-propanedione 1-E-oxime, 2.4 g of 1-bromo-2-propyne, 2.6 g of potassium carbonate and 0.5 g of potassium iodide in 40 ml of acetonitrile is boiled under reflux for 1 hour and then evaporated in vacuo and the residue is dissolved in ethyl acetate. The organic phase is washed twice with water and once with saturated sodium chloride solution, dried with sodium sulfate and evaporated. The crude 1-[4-(3-trifluoromethylphenylmethoxy)-phenyl]-1,2-propanedione 1-E-[(2-propynyl)oxime] thus obtainable is further processed without further purification.

H3e) 1-[4-(3-Trifluoromethylphenylmethoxy)-phenyl]-1,2-propanedione 1-E-[(2-propynyl)oxime]-2-oxime A mixture of 5.9 g of 1-[4-(3-trifluoromethylphenylmethoxy)-phenyl]-1,2-propanedione 1-E-[(2-propynyl)oxime], 2.3 g of hydroxylamine hydrochloride and 2.6 g of pyridine in 60 ml of ethanol is boiled under reflux for 1 hour and then concentrated in vacuo, and 200 ml of water are added to the residue. The product which has precipitated out is filtered off and dissolved in ethyl acetate, and the solution is washed twice with water and once with saturated sodium chloride solution, dried with sodium sulfate and evaporated in vacuo. The residue is suspended in hexane and filtered. 1-[4-(3-Trifluoromethylphenylmethoxy)-phenyl]1,2-propanedione 1-E-[(2-propynyl)oxime]-2-oxime is thus obtained with a melting point of 114–115°.

H3f) Methyl 2-[[[(1-methyl-2-(4-(3-trifluoromethylphenylmethoxy)-phenyl)-2-E-[(2-propynyl)oxyimino]ethylidene)amino]oxy]methyl]-α-(methoxymethylene)-phenylacetate A solution of 5.5 g of 1-[4-(3-trifluoromethylphenylmethoxy)-phenyl]-1,2-propanedione 1-E-[(2-propynyl)oxime]-2-oxime in 25 ml of N,N-dimethylformamide is added dropwise to a suspension of 0.7 g of sodium hydride (about 55% in oil) in 25 ml of N,N-dimethylformamide and the mixture is further stirred at room temperature for 10 minutes. 4 g of methyl 2-(bromomethyl)-α-(methoxymethylene)-phenylacetate in 15 ml of N,N-dimethylformamide are then added dropwise and the reaction mixture is further stirred at room temperature for 1 hour. Thereafter, the mixture is acidified with acetic acid and evaporated in vacuo at 50°. The residue is dissolved in ethyl acetate and the solution is washed twice with water and once with saturated sodium chloride solution, dried with sodium sulfate and evaporated in vacuo. After purification by chromatography (silica gel, ethyl acetate/hexane 1:3), the title compound is obtained as a resin.

Example H4

Methyl 2-[[[(1-methyl-2-(4-(4-chlorophenoxy)-phenyl)-2-E-[(2-ethyl)oxyimino]ethylidene)amino]oxy]methyl]-α-(methoxymethylene)-phenylacetate (compound 1.366)

H4a) 1-[4-(4-Chlorophenoxy)-phenyl]-1,2-propanedione 1-E-oxime 16.7 g of a 30% solution of sodium methylate in methanol are added dropwise to a solution of 22.5 g of 1-[4-(4-chlorophenoxy)-phenyl]-2-propanone and 10.3 g of isopentyl nitrite in 120 ml of methanol at 20–25°, while cooling. The reaction mixture is then further stirred at room temperature for 1 hour. After the solution has been concentrated in vacuo, the residue is dissolved in 300 ml of water and the solution is acidified with 10% hydrochloric acid, the product which precipitates out is filtered off and dissolved in ethyl acetate and the organic phase is washed twice with water, dried with sodium sulfate and evaporated in vacuo. The residue is stirred up in hexane and filtered. The title product is thus obtained with a melting point of 154–155° C.

H4b) 1-[4-(4-Chlorophenoxy)-phenyl]-1,2-propanedione 1-E-[(2-ethyl)oxime]

A mixture of 6 g of) 1-[4-(4-Chlorophenoxy)-phenyl]-1,2-propanedione 1-E-oxime, 3.3 g of ethyl bromide, 3.5 g of potassium carbonate and 0.5 g of potassium iodide in 30 ml of acetonitrile is stirred at 50° for 2 hours, the solvent is then distilled off in vacuo and the residue is dissolved again in ethyl acetate. The organic phase is washed in each case twice with water and saturated sodium chloride solution, dried with sodium sulfate and evaporated in vacuo. After recrystallization of the residue from hexane, the title product is obtained with a melting point of 77–78° C.

H4c) 1-[4-(4-Chlorophenoxy)-phenyl]-1,2-propanedione 1-E-[(2-ethyl)oxime]-2-oxime A mixture of 5.5 g of 1-[4-(4-chlorophenoxy)-phenyl]-1,2-propanedione 1-E-[(2-ethyl)oxime], 2.4 g of hydroxylamine hydrochloride and 2.7 9 of pyridine in 50 ml of ethanol is boiled under reflux for 1 hour and then concentrated in vacuo, and 800 ml of water are added to the residue. The product which has precipitated out is filtered off and dissolved in ethyl acetate and the solution is washed three times with water, dried with sodium sulfate and evaporated in vacuo. The residue is suspended in hexane and filtered. The title product is thus obtained in a pure form with a melting point of 176–177° C.

H4d) Methyl 2-[[[(1-methyl-2-(4-(4-chlorophenoxy)-phenyl)-2-E-[(2-ethyl)oxyimino]ethylidene)amino]oxy] methyl]-α-(methoxymethylene)-phenylacetate.

A solution of 4.7 g of 1-[4-(4-chlorophenoxy)-phenyl]-1, 2-propanedione 1-E-[(2-propynyl)-oxime]-2-oxime in 25 ml of N,N-dimethylformamide is added dropwise to a suspension of 0.65 g of sodium hydride (about 55% in oil) in 20 ml of N,N-dimethylformamide and the mixture is further stirred at room temperature for 10 minutes. 4 g of methyl 2-(bromomethyl)-α-(methoxymethylene)-phenylacetate in 15 ml of N,N-dimethylformamide are then added dropwise and the reaction mixture is further stirred at room temperature for 1 hour. Thereafter, the mixture is acidified with acetic acid and evaporated in vacuo at 50°. The residue is dissolved in ethyl acetate and the solution is washed twice with water and once with saturated sodium chloride solution, dried with sodium sulfate and evaporated in vacuo. After purification by flash chromatography (silica gel, ethyl acetate/hexane 1:3), the title compound is obtained with a melting point of 87–89° C.

Example H5

Methyl 2-[[[(1-methyl-2-(4-(4-chlorophenoxy)-phenyl)-2-E-[(2-ethyl)oxyimino]ethylidene)amino] oxy]methyl]-α-(methoxyimino)-phenylacetate (compound 2.366)

The title compound with a melting point of 90 to 93° C. is obtained in a manner analogous to that described in Example H4 from 1-[4-(4-chlorophenoxy)-phenyl]-1,2-propanedione 1-E-[(2-propynyl)oxime]-2-oxime and methyl 2-(bromomethyl)-α-(methoxyimino)-phenylacetate.

Example H6

2-[[[(1-Methyl-2-(4-(4-chlorophenoxy)-phenyl)-2-E-[(2-ethyl)oxyimino]ethylidene)amino]oxy]methyl]-α-(methoxyimino)-phenylacetic acid methylamide (compound 3.366)

13,3 g of methyl 2-[[[(1-methyl-2-(4-(4-chlorophenoxy)-phenyl)-2-E-[(2-ethyl)oxyimino]ethyliene)amino]oxy] methyl]-α-(methoxyimino)-phenylacetate are left to stand together with 80 ml of dimethylformamide and 9.2 ml of an 8 molar solution of methylamine in ethanol at room temperature for two days. The mixture is concentrated at 50° C., n-hexane is added and the mixture is cooled to room temperature and filtered. The residue is dried under a high vacuum. The title compound is obtained with a melting point of 126–129° C.

Example H7

The other compounds listed in Tables 1 to 3 can also be prepared in a manner analogous to that described in Examples H1 to H6. In the "physical data" column of the tables, the temperatures stated in each case designate the melting point of the compound in question. c.propyl is cyclopropyl.

TABLE 1

Compounds of the general formula

I.1 in which X is CH and Y is oxygen and the combination of substituents $R_2$, $(R_5)_n$ and A—$R_7$ for a compound in each case corresponds to a line in Table A. The compound numbers of the following table correspond to the particular numbers in Table A.

| Compound No. | Phys. Data( Melting point ° C.) |
| --- | --- |
| 1.14 | 75–77° |
| 1.16 | 82–84° |
| 1.22 | 111–113° |
| 1.42 | Resin |
| 1.44 | 91–93° |
| 1.50 | Resin |
| 1.70 | Resin |
| 1.72 | Resin |
| 1.78 | Resin |
| 1.225 | 102–113° |
| 1.226 | 81–83° |
| 1.227 | Resin |
| 1.233 | Resin |
| 1.234 | 73–75° |
| 1.238 | Resin |
| 1.240 | Resin |
| 1.241 | Resin |
| 1.242 | Resin |
| 1.244 | Resin |
| 1.245 | Resin |
| 1.294 | Resin |
| 1.296 | 112–114° |
| 1.366 | 87–89° |

TABLE 2

Compounds of the general formula I.1, in which
X is nitrogen and
Y is oxygen
and the combination of substituents $R_2$, $(R_5)_n$ and A-$R_7$ for a compound in each case corresponds to a line in Table A.

| Compound No. | Melting point (° C.) |
| --- | --- |
| 2.198 | 75–77 |
| 2.254 | 80–82 |
| 2.309 | 106–108 |
| 2.310 | 102–104 |
| 2.366 | 90–93 |

TABLE 3

Compounds of the general formula I.1, in which
X is nitrogen and
Y is NH and
the combination of substituents $R_2$, $(R_5)_n$ and A-$R_7$ for
a compound in each case corresponds to a line in Table A.

| Compound No. | Melting point (° C.) |
|---|---|
| 3.198 | 75–77 |
| 3.254 | 112–114 |
| 3.309 | 89–91 |
| 3.310 | 88–90 |
| 3.366 | 126–129 |

TABLE A

| Compound No. | $R_2$ | $(R_5)_n$ | A-$R_7$ |
|---|---|---|---|
| 1 | $CH_3$ | H | $CH_3$ |
| 2 | $CH_3$ | H | $C_2H_5$ |
| 3 | $CH_3$ | H | n-$C_3H_7$ |
| 4 | $CH_3$ | H | i-$C_3H_7$ |
| 5 | $CH_3$ | H | n-$C_4H_9$ |
| 6 | $CH_3$ | H | n-$C_6H_{13}$ |
| 7 | $CH_3$ | H | $CH_2F$ |
| 8 | $CH_3$ | H | $CHF_2$ |
| 9 | $CH_3$ | H | $CH_2CF_3$ |
| 10 | $CH_3$ | H | $CH_2CH=CH_2$ |
| 11 | $CH_3$ | H | $CH_2CH=CHCH_3$ |
| 12 | $CH_3$ | H | $CH_2CH=C(CH_3)_2$ |
| 13 | $CH_3$ | H | $CH_2CH=CHCl$ |
| 14 | $CH_3$ | H | $CH_2CH=CCl_2$ |
| 15 | $CH_3$ | H | $CH_2C(CH_3)=CH_2$ |
| 16 | $CH_3$ | H | $CH_2C\equiv CH$ |
| 17 | $CH_3$ | H | $CH_2Si(CH_3)_3$ |
| 18 | $CH_3$ | H | $CH_2$-c.propyl-2,2-$Cl_2$ |
| 19 | $CH_3$ | H | $CH_2CN$ |
| 20 | $CH_3$ | H | $CH_2COOC_2H_5$ |
| 21 | $CH_3$ | H | $CH(CH_3)COOC_2H_5$ |
| 22 | $CH_3$ | H | $CH_2C_6H_4$-3-$CF_3$ |
| 23 | $CH_3$ | H | $CH_2C_6H_4$-4-F |
| 24 | $CH_3$ | H | $CH_2C_6H_4$-3-F |
| 25 | $CH_3$ | H | $CH_2C_6H_4$-2-F |
| 26 | $CH_3$ | H | $C(=O)OC_2H_5$ |
| 27 | $CH_3$ | H | $C(=O)NHCH_3$ |
| 28 | $CH_3$ | H | $C(=O)C(=O)OC_2H_5$ |
| 29 | $CH_3$ | 4-F | $CH_3$ |
| 30 | $CH_3$ | 4-F | $C_2H_5$ |
| 31 | $CH_3$ | 4-F | n-$C_3H_7$ |
| 32 | $CH_3$ | 4-F | i-$C_3H_7$ |
| 33 | $CH_3$ | 4-F | n-$C_4H_9$ |
| 34 | $CH_3$ | 4-F | n-$C_6H_{13}$ |
| 35 | $CH_3$ | 4-F | $CH_2F$ |
| 36 | $CH_3$ | 4-F | $CHF_2$ |
| 37 | $CH_3$ | 4-F | $CH_2CF_3$ |
| 38 | $CH_3$ | 4-F | $CH_2CH=CH_2$ |
| 39 | $CH_3$ | 4-F | $CH_2CH=CHCH_3$ |
| 40 | $CH_3$ | 4-F | $CH_2CH=C(CH_3)_2$ |
| 41 | $CH_3$ | 4-F | $CH_2CH=CHCl$ |
| 42 | $CH_3$ | 4-F | $CH_2CH=CCl_2$ |
| 43 | $CH_3$ | 4-F | $CH_2C(CH_3)=CH_2$ |
| 44 | $CH_3$ | 4-F | $CH_2C\equiv CH$ |
| 45 | $CH_3$ | 4-F | $CH_2Si(CH_3)_3$ |
| 46 | $CH_3$ | 4-F | $CH_2$-c.propyl-2,2-$Cl_2$ |
| 47 | $CH_3$ | 4-F | $CH_2CN$ |
| 48 | $CH_3$ | 4-F | $CH_2COOC_2H_5$ |
| 49 | $CH_3$ | 4-F | $CH(CH_3)COOC_2H_5$ |
| 50 | $CH_3$ | 4-F | $CH_2C_6H_4$-3-$CF_3$ |
| 51 | $CH_3$ | 4-F | $CH_2C_6H_4$-4-F |
| 52 | $CH_3$ | 4-F | $CH_2C_6H_4$-3-F |
| 53 | $CH_3$ | 4-F | $CH_2C_6H_4$-2-F |
| 54 | $CH_3$ | 4-F | $C(=O)OC_2H_5$ |
| 55 | $CH_3$ | 4-F | $C(=O)NHCH_3$ |
| 56 | $CH_3$ | 4-F | $C(=O)C(=O)OC_2H_5$ |
| 57 | $CH_3$ | 4-$OCH_3$ | $CH_3$ |
| 58 | $CH_3$ | 4-$OCH_3$ | $C_2H_5$ |
| 59 | $CH_3$ | 4-$OCH_3$ | n-$C_3H_7$ |
| 60 | $CH_3$ | 4-$OCH_3$ | i-$C_3H_7$ |
| 61 | $CH_3$ | 4-$OCH_3$ | n-$C_4H_9$ |
| 62 | $CH_3$ | 4-$OCH_3$ | n-$C_6H_{13}$ |
| 63 | $CH_3$ | 4-$OCH_3$ | $CH_2F$ |
| 64 | $CH_3$ | 4-$OCH_3$ | $CHF_2$ |
| 65 | $CH_3$ | 4-$OCH_3$ | $CH_2CF_3$ |
| 66 | $CH_3$ | 4-$OCH_3$ | $CH_2CH=CH_2$ |
| 67 | $CH_3$ | 4-$OCH_3$ | $CH_2CH=CHCH_3$ |
| 68 | $CH_3$ | 4-$OCH_3$ | $CH_2CH=C(CH_3)_2$ |
| 69 | $CH_3$ | 4-$OCH_3$ | $CH_2CH=CHCl$ |
| 70 | $CH_3$ | 4-$OCH_3$ | $CH_2CH=CCl_2$ |
| 71 | $CH_3$ | 4-$OCH_3$ | $CH_2C(CH_3)=CH_2$ |
| 72 | $CH_3$ | 4-$OCH_3$ | $CH_2C\equiv CH$ |
| 73 | $CH_3$ | 4-$OCH_3$ | $CH_2Si(CH_3)_3$ |
| 74 | $CH_3$ | 4-$OCH_3$ | $CH_2$-c. propyl-2,2-$Cl_2$ |
| 75 | $CH_3$ | 4-$OCH_3$ | $CH_2CN$ |
| 76 | $CH_3$ | 4-$OCH_3$ | $CH_2COOC_2H_5$ |
| 77 | $CH_3$ | 4-$OCH_3$ | $CH(CH_3)COOC_2H_5$ |
| 78 | $CH_3$ | 4-$OCH_3$ | $CH_2C_6H_4$-3-$CF_3$ |
| 79 | $CH_3$ | 4-$OCH_3$ | $CH_2C_6H_4$-4-F |
| 80 | $CH_3$ | 4-$OCH_3$ | $CH_2C_6H_4$-3-F |
| 81 | $CH_3$ | 4-$OCH_3$ | $CH_2C_6H_4$-2-F |
| 82 | $CH_3$ | 4-$OCH_3$ | $C(=O)OC_2H_5$ |
| 83 | $CH_3$ | 4-$OCH_3$ | $C(=O)NHCH_3$ |
| 84 | $CH_3$ | 4-$OCH_3$ | $C(=O)C(=O)OC_2H_5$ |
| 85 | $CH_3$ | 4-$OC_2H_5$ | $CH_3$ |
| 86 | $CH_3$ | 4-$OC_2H_5$ | $C_2H_5$ |
| 87 | $CH_3$ | 4-$OC_2H_5$ | n-$C_3H_7$ |
| 88 | $CH_3$ | 4-$OC_2H_5$ | i-$C_3H_7$ |
| 89 | $CH_3$ | 4-$OC_2H_5$ | n-$C_4H_9$ |
| 90 | $CH_3$ | 4-$OC_2H_5$ | n-$C_6H_{13}$ |
| 91 | $CH_3$ | 4-$OC_2H_5$ | $CH_2F$ |
| 92 | $CH_3$ | 4-$OC_2H_5$ | $CHF_2$ |
| 93 | $CH_3$ | 4-$OC_2H_5$ | $CH_2CF_3$ |
| 94 | $CH_3$ | 4-$OC_2H_5$ | $CH_2CH=CH_2$ |
| 95 | $CH_3$ | 4-$OC_2H_5$ | $CH_2CH=CHCH_3$ |
| 96 | $CH_3$ | 4-$OC_2H_5$ | $CH_2CH=C(CH_3)_2$ |
| 97 | $CH_3$ | 4-$OC_2H_5$ | $CH_2CH=CHCl$ |
| 98 | $CH_3$ | 4-$OC_2H_5$ | $CH_2CH=CCl_2$ |
| 99 | $CH_3$ | 4-$OC_2H_5$ | $CH_2C(CH_3)=CH_2$ |
| 100 | $CH_3$ | 4-$OC_2H_5$ | $CH_2C\equiv CH$ |
| 101 | $CH_3$ | 4-$OC_2H_5$ | $CH_2Si(CH_3)_3$ |
| 102 | $CH_3$ | 4-$OC_2H_5$ | $CH_2$-c.propyl-2,2-$Cl_2$ |
| 103 | $CH_3$ | 4-$OC_2H_5$ | $CH_2CN$ |
| 104 | $CH_3$ | 4-$OC_2H_5$ | $CH_2COOC_2H_5$ |
| 105 | $CH_3$ | 4-$OC_2H_5$ | $CH(CH_3)COOC_2H_5$ |
| 106 | $CH_3$ | 4-$OC_2H_5$ | $CH_2C_6H_4$-3-$CF_3$ |
| 107 | $CH_3$ | 4-$OC_2H_5$ | $CH_2C_6H_4$-4-F |
| 108 | $CH_3$ | 4-$OC_2H_5$ | $CH_2C_6H_4$-3-F |
| 109 | $CH_3$ | 4-$OC_2H_5$ | $CH_2C_6H_4$-2-F |
| 110 | $CH_3$ | 4-$OC_2H_5$ | $C(=O)OC_2H_5$ |
| 111 | $CH_3$ | 4-$OC_2H_5$ | $C(=O)NHCH_3$ |
| 112 | $CH_3$ | 4-$OC_2H_5$ | $C(=O)C(=O)OC_2H_5$ |
| 113 | $CH_3$ | 4-O-n-$C_3H_7$ | $CH_3$ |
| 114 | $CH_3$ | 4-O-n-$C_3H_7$ | $C_2H_5$ |
| 115 | $CH_3$ | 4-O-n-$C_3H_7$ | n-$C_3H_7$ |
| 116 | $CH_3$ | 4-O-n-$C_3H_7$ | i-$C_3H_7$ |
| 117 | $CH_3$ | 4-O-n-$C_3H_7$ | n-$C_4H_9$ |
| 118 | $CH_3$ | 4-O-n-$C_3H_7$ | n-$C_6H_{13}$ |
| 119 | $CH_3$ | 4-O-n-$C_3H_7$ | $CH_2F$ |
| 120 | $CH_3$ | 4-O-n-$C_3H_7$ | $CHF_2$ |
| 121 | $CH_3$ | 4-O-n-$C_3H_7$ | $CH_2CF_3$ |
| 122 | $CH_3$ | 4-O-n-$C_3H_7$ | $CH_2CH=CH_2$ |
| 123 | $CH_3$ | 4-O-n-$C_3H_7$ | $CH_2CH=CHCH_3$ |
| 124 | $CH_3$ | 4-O-n-$C_3H_7$ | $CH_2CH=C(CH_3)_2$ |
| 125 | $CH_3$ | 4-O-n-$C_3H_7$ | $CH_2CH=CHCl$ |
| 126 | $CH_3$ | 4-O-n-$C_3H_7$ | $CH_2CH=CCl_2$ |
| 127 | $CH_3$ | 4-O-n-$C_3H_7$ | $CH_2C(CH_3)=CH_2$ |
| 128 | $CH_3$ | 4-O-n-$C_3H_7$ | $CH_2C\equiv CH$ |
| 129 | $CH_3$ | 4-O-n-$C_3H_7$ | $CH_2Si(CH_3)_3$ |
| 130 | $CH_3$ | 4-O-n-$C_3H_7$ | $CH_2$-c.propyl-2,2-$Cl_2$ |
| 131 | $CH_3$ | 4-O-n-$C_3H_7$ | $CH_2CN$ |
| 132 | $CH_3$ | 4-O-n-$C_3H_7$ | $CH_2COOC_2H_5$ |
| 133 | $CH_3$ | 4-O-n-$C_3H_7$ | $CH(CH_3)COOC_2H_5$ |

TABLE A-continued

| Compound No. | R₂ | (R₅)ₙ | A-R₇ |
|---|---|---|---|
| 134 | CH₃ | 4-O-n-C₃H₇ | CH₂C₆H₄-3-CF₃ |
| 135 | CH₃ | 4-O-n-C₃H₇ | CH₂C₆H₄-4-F |
| 136 | CH₃ | 4-O-n-C₃H₇ | CH₂C₆H₄-3-F |
| 137 | CH₃ | 4-O-n-C₃H₇ | CH₂C₆H₄-2-F |
| 138 | CH₃ | 4-O-n-C₃H₇ | C(=O)OC₂H₅ |
| 139 | CH₃ | 4-O-n-C₃H₇ | C(=O)NHCH₃ |
| 140 | CH₃ | 4-O-n-C₃H₇ | C(=O)C(=O)OC₂H₅ |
| 141 | CH₃ | 2-CH₃ | CH₃ |
| 142 | CH₃ | 2-CH₃ | C₂H₅ |
| 143 | CH₃ | 2-CH₃ | n-C₃H₇ |
| 144 | CH₃ | 2-CH₃ | i-C₃H₇ |
| 145 | CH₃ | 2-CH₃ | n-C₄H₉ |
| 146 | CH₃ | 2-CH₃ | n-C₆H₁₃ |
| 147 | CH₃ | 2-CH₃ | CH₂F |
| 148 | CH₃ | 2-CH₃ | CHF₂ |
| 149 | CH₃ | 2-CH₃ | CH₂CF₃ |
| 150 | CH₃ | 2-CH₃ | CH₂CH=CH₂ |
| 151 | CH₃ | 2-CH₃ | CH₂CH=CHCH₃ |
| 152 | CH₃ | 2-CH₃ | CH₂CH=C(CH₃)₂ |
| 153 | CH₃ | 2-CH₃ | CH₂CH=CHCl |
| 154 | CH₃ | 2-CH₃ | CH₂CH=CCl₂ |
| 155 | CH₃ | 2-CH₃ | CH₂C(CH₃)=CH₂ |
| 156 | CH₃ | 2-CH₃ | CH₂C=CH |
| 157 | CH₃ | 2-CH₃ | CH₂Si(CH₃)₃ |
| 158 | CH₃ | 2-CH₃ | CH₂-c.propyl-2,2-Cl₂ |
| 159 | CH₃ | 2-CH₃ | CH₂CN |
| 160 | CH₃ | 2-CH₃ | CH₂COOC₂H₅ |
| 161 | CH₃ | 2-CH₃ | CH(CH₃)COOC₂H₅ |
| 162 | CH₃ | 2-CH₃ | CH₂C₆H₄-3-CF₃ |
| 163 | CH₃ | 2-CH₃ | CH₂C₆H₄-4-F |
| 164 | CH₃ | 2-CH₃ | CH₂C₆H₄-3-F |
| 165 | CH₃ | 2-CH₃ | CH₂C₆H₄-2-F |
| 166 | CH₃ | 2-CH₃ | C(=O)OC₂H₅ |
| 167 | CH₃ | 2-CH₃ | C(=O)NHCH₃ |
| 168 | CH₃ | 2-CH₃ | C(=O)C(=O)OC₂H₅ |
| 169 | CH₃ | 4-OCH₂Si(CH₃)₃ | CH₃ |
| 170 | CH₃ | 4-OCH₂Si(CH₃)₃ | C₂H₅ |
| 171 | CH₃ | 4-OCH₂Si(CH₃)₃ | n-C₃H₇ |
| 172 | CH₃ | 4-OCH₂Si(CH₃)₃ | i-C₃H₇ |
| 173 | CH₃ | 4-OCH₂Si(CH₃)₃ | n-C₄H₉ |
| 174 | CH₃ | 4-OCH₂Si(CH₃)₃ | n-C₆H₁₃ |
| 175 | CH₃ | 4-OCH₂Si(CH₃)₃ | CH₂F |
| 176 | CH₃ | 4-OCH₂Si(CH₃)₃ | CHF₂ |
| 177 | CH₃ | 4-OCH₂Si(CH₃)₃ | CH₂CF₃ |
| 178 | CH₃ | 4-OCH₂Si(CH₃)₃ | CH₂CH=CH₂ |
| 179 | CH₃ | 4-OCH₂Si(CH₃)₃ | CH₂CH=CHCH₃ |
| 180 | CH₃ | 4-OCH₂Si(CH₃)₃ | CH₂CH=C(CH₃)₂ |
| 181 | CH₃ | 4-OCH₂Si(CH₃)₃ | CH₂CH=CHCl |
| 182 | CH₃ | 4-OCH₂Si(CH₃)₃ | CH₂CH=CCl₂ |
| 183 | CH₃ | 4-OCH₂Si(CH₃)₃ | CH₂C(CH₃)=CH₂ |
| 184 | CH₃ | 4-OCH₂Si(CH₃)₃ | CH₂C=CH |
| 185 | CH₃ | 4-OCH₂Si(CH₃)₃ | CH₂Si(CH₃)₃ |
| 186 | CH₃ | 4-OCH₂Si(CH₃)₃ | CH₂-c.propyl-2,2-Cl₂ |
| 187 | CH₃ | 4-OCH₂Si(CH₃)₃ | CH₂CN |
| 188 | CH₃ | 4-OCH₂Si(CH₃)₃ | CH₂COOC₂H₅ |
| 189 | CH₃ | 4-OCH₂Si(CH₃)₃ | CH(CH₃)COOC₂H₅ |
| 190 | CH₃ | 4-OCH₂Si(CH₃)₃ | CH₂C₆H₄-3-CF₃ |
| 191 | CH₃ | 4-OCH₂Si(CH₃)₃ | CH₂C₆H₄-4-F |
| 192 | CH₃ | 4-OCH₂Si(CH₃)₃ | CH₂C₆H₄-3-F |
| 193 | CH₃ | 4-OCH₂Si(CH₃)₃ | CH₂C₆H₄-2-F |
| 194 | CH₃ | 4-OCH₂Si(CH₃)₃ | C(=O)OC₂H₅ |
| 195 | CH₃ | 4-OCH₂Si(CH₃)₃ | C(=O)NHCH₃ |
| 196 | CH₃ | 4-OCH₂Si(CH₃)₃ | C(=O)C(=O)OC₂H₅ |
| 197 | CH₃ | 4-OCH₂C₆H₄-4-CF₃ | CH₃ |
| 198 | CH₃ | 4-OCH₂C₆H₄-4-CF₃ | C₂H₅ |
| 199 | CH₃ | 4-OCH₂C₆H₄-4-CF₃ | n-C₃H₇ |
| 200 | CH₃ | 4-OCH₂C₆H₄-4-CF₃ | i-C₃H₇ |
| 201 | CH₃ | 4-OCH₂C₆H₄-4-CF₃ | n-C₄H₉ |
| 202 | CH₃ | 4-OCH₂C₆H₄-4-CF₃ | n-C₆H₁₃ |
| 203 | CH₃ | 4-OCH₂C₆H₄-4-CF₃ | CH₂F |
| 204 | CH₃ | 4-OCH₂C₆H₄-4-CF₃ | CHF₂ |
| 205 | CH₃ | 4-OCH₂C₆H₄-4-CF₃ | CH₂CF₃ |
| 206 | CH₃ | 4-OCH₂C₆H₄-4-CF₃ | CH₂CH=CH₂ |
| 207 | CH₃ | 4-OCH₂C₆H₄-4-CF₃ | CH₂CH=CHCH₃ |
| 208 | CH₃ | 4-OCH₂C₆H₄-4-CF₃ | CH₂CH=C(CH₃)₂ |
| 209 | CH₃ | 4-OCH₂C₆H₄-4-CF₃ | CH₂CH=CHCl |
| 210 | CH₃ | 4-OCH₂C₆H₄-4-CF₃ | CH₂CH=CCl₂ |
| 211 | CH₃ | 4-OCH₂C₆H₄-4-CF₃ | CH₂C(CH₃)=CH₂ |
| 212 | CH₃ | 4-OCH₂C₆H₄-4-CF₃ | CH₂C=CH |
| 213 | CH₃ | 4-OCH₂C₆H₄-4-CF₃ | CH₂Si(CH₃)₃ |
| 214 | CH₃ | 4-OCH₂C₆H₄-4-CF₃ | CH₂-c.propyl-2,2-Cl₂ |
| 215 | CH₃ | 4-OCH₂C₆H₄-4-CF₃ | CH₂CN |
| 216 | CH₃ | 4-OCH₂C₆H₄-4-CF₃ | CH₂COOC₂H₅ |
| 217 | CH₃ | 4-OCH₂C₆H₄-4-CF₃ | CH(CH₃)COOC₂H₅ |
| 218 | CH₃ | 4-OCH₂C₆H₄-4-CF₃ | CH₂C₆H₄-3-CF₃ |
| 219 | CH₃ | 4-OCH₂C₆H₄-4-CF₃ | CH₂C₆H₄-4-F |
| 220 | CH₃ | 4-OCH₂C₆H₄-4-CF₃ | CH₂C₆H₄-3-F |
| 221 | CH₃ | 4-OCH₂C₆H₄-4-CF₃ | CH₂C₆H₄-2-F |
| 222 | CH₃ | 4-OCH₂C₆H₄-4-CF₃ | C(=O)OC₂H₅ |
| 223 | CH₃ | 4-OCH₂C₆H₄-4-CF₃ | C(=O)NHCH₃ |
| 224 | CH₃ | 4-OCH₂C₆H₄-4-CF₃ | C(=O)C(=O)OC₂H₅ |
| 225 | CH₃ | 4-OCH₂C₆H₄-3-CF₃ | CH₃ |
| 226 | CH₃ | 4-OCH₂C₆H₄-3-CF₃ | C₂H₅ |
| 227 | CH₃ | 4-OCH₂C₆H₄-3-CF₃ | n-C₃H₇ |
| 228 | CH₃ | 4-OCH₂C₆H₄-3-CF₃ | i-C₃H₇ |
| 229 | CH₃ | 4-OCH₂C₆H₄-3-CF₃ | n-C₄H₉ |
| 230 | CH₃ | 4-OCH₂C₆H₄-3-CF₃ | n-C₆H₁₃ |
| 231 | CH₃ | 4-OCH₂C₆H₄-3-CF₃ | CH₂F |
| 232 | CH₃ | 4-OCH₂C₆H₄-3-CF₃ | CHF₂ |
| 233 | CH₃ | 4-OCH₂C₆H₄-3-CF₃ | CH₂CF₃ |
| 234 | CH₃ | 4-OCH₂C₆H₄-3-CF₃ | CH₂CH=CH₂ |
| 235 | CH₃ | 4-OCH₂C₆H₄-3-CF₃ | CH₂CH=CHCH₃ |
| 236 | CH₃ | 4-OCH₂C₆H₄-3-CF₃ | CH₂CH=C(CH₃)₂ |
| 237 | CH₃ | 4-OCH₂C₆H₄-3-CF₃ | CH₂CH=CHCl |
| 238 | CH₃ | 4-OCH₂C₆H₄-3-CF₃ | CH₂CH=CCl₂ |
| 239 | CH₃ | 4-OCH₂C₆H₄-3-CF₃ | CH₂C(CH₃)=CH₂ |
| 240 | CH₃ | 4-OCH₂C₆H₄-3-CF₃ | CH₂C=CH |
| 241 | CH₃ | 4-OCH₂C₆H₄-3-CF₃ | CH₂Si(CH₃)₃ |
| 242 | CH₃ | 4-OCH₂C₆H₄-3-CF₃ | CH₂-c.propyl-2,2-Cl₂ |
| 243 | CH₃ | 4-OCH₂C₆H₄-3-CF₃ | CH₂CN |
| 244 | CH₃ | 4-OCH₂C₆H₄-3-CF₃ | CH₂COOC₂H₅ |
| 245 | CH₃ | 4-OCH₂C₆H₄-3-CF₃ | CH(CH₃)COOC₂H₅ |
| 246 | CH₃ | 4-OCH₂C₆H₄-3-CF₃ | CH₂C₆H₄-3-CF₃ |
| 247 | CH₃ | 4-OCH₂C₆H₄-3-CF₃ | CH₂C₆H₄-4-F |
| 248 | CH₃ | 4-OCH₂C₆H₄-3-CF₃ | CH₂C₆H₄-3-F |
| 249 | CH₃ | 4-OCH₂C₆H₄-3-CF₃ | CH₂C₆H₄-2-F |
| 250 | CH₃ | 4-OCH₂C₆H₄-3-CF₃ | C(=O)OC₂H₅ |
| 251 | CH₃ | 4-OCH₂C₆H₄-3-CF₃ | C(=O)NHCH₃ |
| 252 | CH₃ | 4-OCH₂C₆H₄-3-CF₃ | C(=O)C(=O)OC₂H₅ |
| 253 | CH₃ | 4-OCH₂C₆H₄-2-CF₃ | CH₃ |
| 254 | CH₃ | 4-OCH₂C₆H₄-2-CF₃ | C₂H₅ |
| 255 | CH₃ | 4-OCH₂C₆H₄-2-CF₃ | n-C₃H₇ |
| 256 | CH₃ | 4-OCH₂C₆H₄-2-CF₃ | i-C₃H₇ |
| 257 | CH₃ | 4-OCH₂C₆H₄-2-CF₃ | n-C₄H₉ |
| 258 | CH₃ | 4-OCH₂C₆H₄-2-CF₃ | n-C₆H₁₃ |
| 259 | CH₃ | 4-OCH₂C₆H₄-2-CF₃ | CH₂F |
| 260 | CH₃ | 4-OCH₂C₆H₄-2-CF₃ | CHF₂ |
| 261 | CH₃ | 4-OCH₂C₆H₄-2-CF₃ | CH₂CF₃ |
| 262 | CH₃ | 4-OCH₂C₆H₄-2-CF₃ | CH₂CH=CH₂ |
| 263 | CH₃ | 4-OCH₂C₆H₄-2-CF₃ | CH₂CH=CHCH₃ |
| 264 | CH₃ | 4-OCH₂C₆H₄-2-CF₃ | CH₂CH=C(CH₃)₂ |
| 265 | CH₃ | 4-OCH₂C₆H₄-2-CF₃ | CH₂CH=CHCl |
| 266 | CH₃ | 4-OCH₂C₆H₄-2-CF₃ | CH₂CH=CCl₂ |
| 267 | CH₃ | 4-OCH₂C₆H₄-2-CF₃ | CH₂C(CH₃)=CH₂ |
| 268 | CH₃ | 4-OCH₂C₆H₄-2-CF₃ | CH₂C=CH |
| 269 | CH₃ | 4-OCH₂C₆H₄-2-CF₃ | CH₂Si(CH₃)₃ |
| 270 | CH₃ | 4-OCH₂C₆H₄-2-CF₃ | CH₂-c.propyl-2,2-Cl₂ |
| 271 | CH₃ | 4-OCH₂C₆H₄-2-CF₃ | CH₂CN |
| 272 | CH₃ | 4-OCH₂C₆H₄-2-CF₃ | CH₂COOC₂H₅ |
| 273 | CH₃ | 4-OCH₂C₆H₄-2-CF₃ | CH(CH₃)COOC₂H₅ |
| 274 | CH₃ | 4-OCH₂C₆H₄-2-CF₃ | CH₂C₆H₄-3-CF₃ |
| 275 | CH₃ | 4-OCH₂C₆H₄-2-CF₃ | CH₂C₆H₄-4-F |
| 276 | CH₃ | 4-OCH₂C₆H₄-2-CF₃ | CH₂C₆H₄-3-F |
| 277 | CH₃ | 4-OCH₂C₆H₄-2-CF₃ | CH₂C₆H₄-2-F |
| 278 | CH₃ | 4-OCH₂C₆H₄-2-CF₃ | C(=O)OC₂H₅ |
| 279 | CH₃ | 4-OCH₂C₆H₄-2-CF₃ | C(=O)NHCH₃ |
| 280 | CH₃ | 4-OCH₂C₆H₄-2-CF₃ | C(=O)C(=O)OC₂H₅ |
| 281 | CH₃ | 4-OCH₂C₆H₄-4-F | CH₃ |
| 282 | CH₃ | 4-OCH₂C₆H₄-4-F | C₂H₅ |
| 283 | CH₃ | 4-OCH₂C₆H₄-4-F | n-C₃H₇ |
| 284 | CH₃ | 4-OCH₂C₆H₄-4-F | i-C₃H₇ |
| 285 | CH₃ | 4-OCH₂C₆H₄-4-F | n-C₄H₉ |

TABLE A-continued

| Compound No. | R₂ | (R₅)ₙ | A-R₇ |
|---|---|---|---|
| 286 | $CH_3$ | 4-$OCH_2C_6H_4$-4-F | n-$C_6H_{13}$ |
| 287 | $CH_3$ | 4-$OCH_2C_6H_4$-4-F | $CH_2F$ |
| 288 | $CH_3$ | 4-$OCH_2C_6H_4$-4-F | $CHF_2$ |
| 289 | $CH_3$ | 4-$OCH_2C_6H_4$-4-F | $CH_2CF_3$ |
| 290 | $CH_3$ | 4-$OCH_2C_6H_4$-4-F | $CH_2CH=CH_2$ |
| 291 | $CH_3$ | 4-$OCH_2C_6H_4$-4-F | $CH_2CH=CHCH_3$ |
| 292 | $CH_3$ | 4-$OCH_2C_6H_4$-4-F | $CH_2CH=C(CH_3)_2$ |
| 293 | $CH_3$ | 4-$OCH_2C_6H_4$-4-F | $CH_2CH=CHCl$ |
| 294 | $CH_3$ | 4-$OCH_2C_6H_4$-4-F | $CH_2CH=CCl_2$ |
| 295 | $CH_3$ | 4-$OCH_2C_6H_4$-4-F | $CH_2C(CH_3)=CH_2$ |
| 296 | $CH_3$ | 4-$OCH_2C_6H_4$-4-F | $CH_2C=CH$ |
| 297 | $CH_3$ | 4-$OCH_2C_6H_4$-4-F | $CH_2Si(CH_3)_3$ |
| 298 | $CH_3$ | 4-$OCH_2C_6H_4$-4-F | $CH_2$-c.propyl-2,2-$Cl_2$ |
| 299 | $CH_3$ | 4-$OCH_2C_6H_4$-4-F | $CH_2CN$ |
| 300 | $CH_3$ | 4-$OCH_2C_6H_4$-4-F | $CH_2COOC_2H_5$ |
| 301 | $CH_3$ | 4-$OCH_2C_6H_4$-4-F | $CH(CH_3)COOC_2H_5$ |
| 302 | $CH_3$ | 4-$OCH_2C_6H_4$-4-F | $CH_2C_6H_4$-3-$CF_3$ |
| 303 | $CH_3$ | 4-$OCH_2C_6H_4$-4-F | $CH_2C_6H_4$-4-F |
| 304 | $CH_3$ | 4-$OCH_2C_6H_4$-4-F | $CH_2C_6H_4$-3-F |
| 305 | $CH_3$ | 4-$OCH_2C_6H_4$-4-F | $CH_2C_6H_4$-2-F |
| 306 | $CH_3$ | 4-$OCH_2C_6H_4$-4-F | $C(=O)OC_2H_5$ |
| 307 | $CH_3$ | 4-$OCH_2C_6H_4$-4-F | $C(=O)NHCH_3$ |
| 308 | $CH_3$ | 4-$OCH_2C_6H_4$-4-F | $C(=O)C(=O)OC_2H_5$ |
| 309 | $CH_3$ | 4-$OC_6H_4$3-$CF_3$ | $CH_3$ |
| 310 | $CH_3$ | 4-$OC_6H_4$3-$CF_3$ | $C_2H_5$ |
| 311 | $CH_3$ | 4-$OC_6H_4$3-$CF_3$ | n-$C_3H_7$ |
| 312 | $CH_3$ | 4-$OC_6H_4$3-$CF_3$ | i-$C_3H_7$ |
| 313 | $CH_3$ | 4-$OC_6H_4$3-$CF_3$ | n-$C_4H_9$ |
| 314 | $CH_3$ | 4-$OC_6H_4$3-$CF_3$ | n-$C_6H_{13}$ |
| 315 | $CH_3$ | 4-$OC_6H_4$3-$CF_3$ | $CH_2F$ |
| 316 | $CH_3$ | 4-$OC_6H_4$3-$CF_3$ | $CHF_2$ |
| 317 | $CH_3$ | 4-$OC_6H_4$3-$CF_3$ | $CH_2CF_3$ |
| 318 | $CH_3$ | 4-$OC_6H_4$3-$CF_3$ | $CH_2CH=CH_2$ |
| 319 | $CH_3$ | 4-$OC_6H_4$3-$CF_3$ | $CH_2CH=CHCH_3$ |
| 320 | $CH_3$ | 4-$OC_6H_4$3-$CF_3$ | $CH_2CH=C(CH_3)_2$ |
| 321 | $CH_3$ | 4-$OC_6H_4$3-$CF_3$ | $CH_2CH=CHCl$ |
| 322 | $CH_3$ | 4-$OC_6H_4$3-$CF_3$ | $CH_2CH=CCl_2$ |
| 323 | $CH_3$ | 4-$OC_6H_4$3-$CF_3$ | $CH_2C(CH_3)=CH_2$ |
| 324 | $CH_3$ | 4-$OC_6H_4$3-$CF_3$ | $CH_2C=CH$ |
| 325 | $CH_3$ | 4-$OC_6H_4$3-$CF_3$ | $CH_2Si(CH_3)_3$ |
| 326 | $CH_3$ | 4-$OC_6H_4$3-$CF_3$ | $CH_2$-c.propyl-2,2-$Cl_2$ |
| 327 | $CH_3$ | 4-$OC_6H_4$3-$CF_3$ | $CH_2CN$ |
| 328 | $CH_3$ | 4-$OC_6H_4$3-$CF_3$ | $CH_2COOC_2H_5$ |
| 329 | $CH_3$ | 4-$OC_6H_4$3-$CF_3$ | $CH(CH_3)COOC_2H_5$ |
| 330 | $CH_3$ | 4-$OC_6H_4$3-$CF_3$ | $CH_2C_6H_4$-3-$CF_3$ |
| 331 | $CH_3$ | 4-$OC_6H_4$3-$CF_3$ | $CH_2C_6H_4$-4-F |
| 332 | $CH_3$ | 4-$OC_6H_4$3-$CF_3$ | $CH_2C_6H_4$-3-F |
| 333 | $CH_3$ | 4-$OC_6H_4$3-$CF_3$ | $CH_2C_6H_4$-2-F |
| 334 | $CH_3$ | 4-$OC_6H_4$3-$CF_3$ | $C(=O)OC_2H_5$ |
| 335 | $CH_3$ | 4-$OC_6H_4$3-$CF_3$ | $C(=O)NHCH_3$ |
| 336 | $CH_3$ | 4-$OC_6H_4$3-$CF_3$ | $C(=O)C(=O)OC_2H_5$ |
| 337 | $C_2H_5$ | 4-$OCH_2C_6H_4$-3-$CF_3$ | $CH_3$ |
| 338 | $C_2H_5$ | 4-$OCH_2C_6H_4$-3-$CF_3$ | $C_2H_5$ |
| 339 | $C_2H_5$ | 4-$OCH_2C_6H_4$-3-$CF_3$ | n-$C_3H_7$ |
| 340 | $C_2H_5$ | 4-$OCH_2C_6H_4$-3-$CF_3$ | i-$C_3H_7$ |
| 341 | $C_2H_5$ | 4-$OCH_2C_6H_4$-3-$CF_3$ | n-$C_4H_9$ |
| 342 | $C_2H_5$ | 4-$OCH_2C_6H_4$-3-$CF_3$ | n-$C_6H_{13}$ |
| 343 | $C_2H_5$ | 4-$OCH_2C_6H_4$-3-$CF_3$ | $CH_2F$ |
| 344 | $C_2H_5$ | 4-$OCH_2C_6H_4$-3-$CF_3$ | $CHF_2$ |
| 345 | $C_2H_5$ | 4-$OCH_2C_6H_4$-3-$CF_3$ | $CH_2CF_3$ |
| 346 | $C_2H_5$ | 4-$OCH_2C_6H_4$-3-$CF_3$ | $CH_2CH=CH_2$ |
| 347 | $C_2H_5$ | 4-$OCH_2C_6H_4$-3-$CF_3$ | $CH_2CH=CHCH_3$ |
| 348 | $C_2H_5$ | 4-$OCH_2C_6H_4$-3-$CF_3$ | $CH_2CH=C(CH_3)_2$ |
| 349 | $C_2H_5$ | 4-$OCH_2C_6H_4$-3-$CF_3$ | $CH_2CH=CHCl$ |
| 350 | $C_2H_5$ | 4-$OCH_2C_6H_4$-3-$CF_3$ | $CH_2CH=CCl_2$ |
| 351 | $C_2H_5$ | 4-$OCH_2C_6H_4$-3-$CF_3$ | $CH_2C(CH_3)=CH_2$ |
| 352 | $C_2H_5$ | 4-$OCH_2C_6H_4$-3-$CF_3$ | $CH_2C=CH$ |
| 353 | $C_2H_5$ | 4-$OCH_2C_6H_4$-3-$CF_3$ | $CH_2Si(CH_3)_3$ |
| 354 | $C_2H_5$ | 4-$OCH_2C_6H_4$-3-$CF_3$ | $CH_2$-c.propyl-2,2-$Cl_2$ |
| 355 | $C_2H_5$ | 4-$OCH_2C_6H_4$-3-$CF_3$ | $CH_2CN$ |
| 356 | $C_2H_5$ | 4-$OCH_2C_6H_4$-3-$CF_3$ | $CH_2COOC_2H_5$ |
| 357 | $C_2H_5$ | 4-$OCH_2C_6H_4$-3-$CF_3$ | $CH(CH_3)COOC_2H_5$ |
| 358 | $C_2H_5$ | 4-$OCH_2C_6H_4$-3-$CF_3$ | $CH_2C_6H_4$-3-$CF_3$ |
| 359 | $C_2H_5$ | 4-$OCH_2C_6H_4$-3-$CF_3$ | $CH_2C_6H_4$-4-F |
| 360 | $C_2H_5$ | 4-$OCH_2C_6H_4$-3-$CF_3$ | $CH_2C_6H_4$-3-F |
| 361 | $C_2H_5$ | 4-$OCH_2C_6H_4$-3-$CF_3$ | $CH_2C_6H_4$-2-F |
| 362 | $C_2H_5$ | 4-$OC_6H_4$-3-$CF_3$ | $C(=O)OC_2H_5$ |
| 363 | $C_2H_5$ | 4-$OCH_2C_6H_4$-3-$CF_3$ | $C(=O)NHCH_3$ |
| 364 | $C_2H_5$ | 4-$OCH_2C_6H_4$-3-$CF_3$ | $C(=O)C(=O)OC_2H_5$ |
| 365 | $CH_3$ | 4-$OC_6H_4$-4-Cl | $CH_3$ |
| 366 | $CH_3$ | 4-$OC_6H_4$-4-Cl | $C_2H_5$ |
| 367 | $CH_3$ | 4-$OC_6H_4$-4-Cl | n-$C_3H_7$ |
| 368 | $CH_3$ | 4-$OC_6H_4$-4-Cl | i-$C_3H_7$ |
| 369 | $CH_3$ | 4-$OC_6H_4$-4-Cl | n-$C_4H_9$ |
| 370 | $CH_3$ | 4-$OC_6H_4$-4-Cl | n-$C_6H_{13}$ |
| 371 | $CH_3$ | 4-$OC_6H_4$-4-Cl | $CH_2F$ |
| 372 | $CH_3$ | 4-$OC_6H_4$-4-Cl | $CHF_2$ |
| 373 | $CH_3$ | 4-$OC_6H_4$-4-Cl | $CH_2CF_3$ |
| 374 | $CH_3$ | 4-$OC_6H_4$-4-Cl | $CH_2CH=CH_2$ |
| 375 | $CH_3$ | 4-$OC_6H_4$-4-Cl | $CH_2CH=CHCH_3$ |
| 376 | $CH_3$ | 4-$OC_6H_4$-4-Cl | $CH_2CH=C(CH_3)_2$ |
| 377 | $CH_3$ | 4-$OC_6H_4$-4-Cl | $CH_2CH=CHCl$ |
| 378 | $CH_3$ | 4-$OC_6H_4$-4-Cl | $CH_2CH=CCl_2$ |
| 379 | $CH_3$ | 4-$OC_6H_4$-4-Cl | $CH_2C(CH_3)=CH_2$ |
| 380 | $CH_3$ | 4-$OC_6H_4$-4-Cl | $CH_2C=CH$ |
| 381 | $CH_3$ | 4-$OC_6H_4$-4-Cl | $CH_2Si(CH_3)_3$ |
| 382 | $CH_3$ | 4-$OC_6H_4$-4-Cl | $CH_2$-c.propyl-2,2-$Cl_2$ |
| 383 | $CH_3$ | 4-$OC_6H_4$-4-Cl | $CH_2CN$ |
| 384 | $CH_3$ | 4-$OC_6H_4$-4-Cl | $CH_2COOC_2H_5$ |
| 385 | $CH_3$ | 4-$OC_6H_4$-4-Cl | $CH(CH_3)COOC_2H_5$ |
| 386 | $CH_3$ | 4-$OC_6H_4$-4-Cl | $CH_2C_6H_4$-3-$CF_3$ |
| 387 | $CH_3$ | 4-$OC_6H_4$-4-Cl | $CH_2C_6H_4$-4-F |
| 388 | $CH_3$ | 4-$OC_6H_4$-4-Cl | $CH_2C_6H_4$-3-F |
| 389 | $CH_3$ | 4-$OC_6H_4$-4-Cl | $CH_2C_6H_4$-2-F |
| 390 | $CH_3$ | 4-$OC_6H_4$-4-Cl | $C(=O)OC_2H_5$ |
| 391 | $CH_3$ | 4-$OC_6H_4$-4-Cl | $C(=O)NHCH_3$ |
| 392 | $CH_3$ | 4-$OC_6H_4$-4-Cl | $C(=O)C(=O)OC_2H_5$ |
| 393 | $CH_3$ | 4-$OC_6H_4$-3-Cl | $CH_3$ |
| 394 | $CH_3$ | 4-$OC_6H_4$-3-Cl | $C_2H_5$ |
| 395 | $CH_3$ | 4-$OC_6H_4$-3-Cl | n-$C_3H_7$ |
| 396 | $CH_3$ | 4-$OC_6H_4$-3-Cl | i-$C_3H_7$ |
| 397 | $CH_3$ | 4-$OC_6H_4$-3-Cl | n-$C_4H_9$ |
| 398 | $CH_3$ | 4-$OC_6H_4$-3-Cl | n-$C_6H_{13}$ |
| 399 | $CH_3$ | 4-$OC_6H_4$-3-Cl | $CH_2F$ |
| 400 | $CH_3$ | 4-$OC_6H_4$-3-Cl | $CHF_2$ |
| 401 | $CH_3$ | 4-$OC_6H_4$-3-Cl | $CH_2CF_3$ |
| 402 | $CH_3$ | 4-$OC_6H_4$-3-Cl | $CH_2CH=CH_2$ |
| 403 | $CH_3$ | 4-$OC_6H_4$-3-Cl | $CH_2CH=CHCH_3$ |
| 404 | $CH_3$ | 4-$OC_6H_4$-3-Cl | $CH_2CH=C(CH_3)_2$ |
| 405 | $CH_3$ | 4-$OC_6H_4$-3-Cl | $CH_2CH=CHCl$ |
| 406 | $CH_3$ | 4-$OC_6H_4$-3-Cl | $CH_2CH=CCl_2$ |
| 407 | $CH_3$ | 4-$OC_6H_4$-3-Cl | $CH_2C(CH_3)=CH_2$ |
| 408 | $CH_3$ | 4-$OC_6H_4$-3-Cl | $CH_2C=CH$ |
| 409 | $CH_3$ | 4-$OC_6H_4$-3-Cl | $CH_2Si(CH_3)_3$ |
| 410 | $CH_3$ | 4-$OC_6H_4$-3-Cl | $CH_2$-c.propyl-2,2-$Cl_2$ |
| 411 | $CH_3$ | 4-$OC_6H_4$-3-Cl | $CH_2CN$ |
| 412 | $CH_3$ | 4-$OC_6H_4$-3-Cl | $CH_2COOC_2H_5$ |
| 413 | $CH_3$ | 4-$OC_6H_4$-3-Cl | $CH(CH_3)COOC_2H_5$ |
| 414 | $CH_3$ | 4-$OC_6H_4$-3-Cl | $CH_2C_6H_4$-3-$CF_3$ |
| 415 | $CH_3$ | 4-$OC_6H_4$-3-Cl | $CH_2C_6H_4$-4-F |
| 416 | $CH_3$ | 4-$OC_6H_4$-3-Cl | $CH_2C_6H_4$-3-F |
| 417 | $CH_3$ | 4-$OC_6H_4$-3-Cl | $CH_2C_6H_4$-2-F |
| 418 | $CH_3$ | 4-$OC_6H_4$-3-Cl | $C(=O)OC_2H_5$ |
| 419 | $CH_3$ | 4-$OC_6H_4$-3-Cl | $C(=O)NHCH_3$ |
| 420 | $CH_3$ | 4-$OC_6H_4$-3-Cl | $C(=O)C(=O)OC_2H_5$ |
| 421 | $CH_3$ | 4-$OC_6H_4$-2-Cl | $CH_3$ |
| 422 | $CH_3$ | 4-$OC_6H_4$-2-Cl | $C_2H_5$ |
| 423 | $CH_3$ | 4-$OC_6H_4$-2-Cl | n-$C_3H_7$ |
| 424 | $CH_3$ | 4-$OC_6H_4$-2-Cl | i-$C_3H_7$ |
| 425 | $CH_3$ | 4-$OC_6H_4$-2-Cl | n-$C_4H_9$ |
| 426 | $CH_3$ | 4-$OC_6H_4$-2-Cl | n-$C_6H_{13}$ |
| 427 | $CH_3$ | 4-$OC_6H_4$-2-Cl | $CH_2F$ |
| 428 | $CH_3$ | 4-$OC_6H_4$-2-Cl | $CHF_2$ |
| 429 | $CH_3$ | 4-$OC_6H_4$-2-Cl | $CH_2CF_3$ |
| 430 | $CH_3$ | 4-$OC_6H_4$-2-Cl | $CH_2CH=CH_2$ |
| 431 | $CH_3$ | 4-$OC_6H_4$-2-Cl | $CH_2CH=CHCH_3$ |
| 432 | $CH_3$ | 4-$OC_6H_4$-2-Cl | $CH_2CH=C(CH_3)_2$ |
| 433 | $CH_3$ | 4-$OC_6H_4$-2-Cl | $CH_2CH=CHCl$ |
| 434 | $CH_3$ | 4-$OC_6H_4$-2-Cl | $CH_2CH=CCl_2$ |
| 435 | $CH_3$ | 4-$OC_6H_4$-2-Cl | $CH_2C(CH_3)=CH_2$ |
| 436 | $CH_3$ | 4-$OC_6H_4$-2-Cl | $CH_2C=CH$ |
| 437 | $CH_3$ | 4-$OC_6H_4$-2-Cl | $CH_2Si(CH_3)_3$ |

TABLE A-continued

| Compound No. | R₂ | (R₅)ₙ | A-R₇ |
|---|---|---|---|
| 438 | $CH_3$ | 4-$OC_6H_4$-2-Cl | $CH_2$-c.propyl-2,2-$Cl_2$ |
| 439 | $CH_3$ | 4-$OC_6H_4$-2-Cl | $CH_2CN$ |
| 440 | $CH_3$ | 4-$OC_6H_4$-2-Cl | $CH_2COOC_2H_5$ |
| 441 | $CH_3$ | 4-$OC_6H_4$-2-Cl | $CH(CH_3)COOC_2H_5$ |
| 442 | $CH_3$ | 4-$OC_6H_4$-2-Cl | $CH_2C_6H_4$-3-$CF_3$ |
| 443 | $CH_3$ | 4-$OC_6H_4$-2-Cl | $CH_2C_6H_4$-4-F |
| 444 | $CH_3$ | 4-$OC_6H_4$-2-Cl | $CH_2C_6H_4$-3-F |
| 445 | $CH_3$ | 4-$OC_6H_4$-2-Cl | $CH_2C_6H_4$-2-F |
| 446 | $CH_3$ | 4-$OC_6H_4$-2-Cl | $C(=O)OC_2H_5$ |
| 447 | $CH_3$ | 4-$OC_6H_4$-2-Cl | $C(=O)NHCH_3$ |
| 448 | $CH_3$ | 4-$OC_6H_4$-2-Cl | $C(=O)C(=O)OC_2H_5$ |
| 449 | $CH_3$ | 4-$OC_6H_4$-4-F | $CH_3$ |
| 450 | $CH_3$ | 4-$OC_6H_4$-4-F | $C_2H_5$ |
| 451 | $CH_3$ | 4-$OC_6H_4$-4-F | n-$C_3H_7$ |
| 452 | $CH_3$ | 4-$OC_6H_4$-4-F | i-$C_3H_7$ |
| 453 | $CH_3$ | 4-$OC_6H_4$-4-F | n-$C_4H_9$ |
| 454 | $CH_3$ | 4-$OC_6H_4$-4-F | n-$C_6H_{13}$ |
| 455 | $CH_3$ | 4-$OC_6H_4$-4-F | $CH_2F$ |
| 456 | $CH_3$ | 4-$OC_6H_4$-4-F | $CHF_2$ |
| 457 | $CH_3$ | 4-$OC_6H_4$-4-F | $CH_2CF_3$ |
| 458 | $CH_3$ | 4-$OC_6H_4$-4-F | $CH_2CH=CH_2$ |
| 459 | $CH_3$ | 4-$OC_6H_4$-4-F | $CH_2CH=CHCH_3$ |
| 460 | $CH_3$ | 4-$OC_6H_4$-4-F | $CH_2CH=C(CH_3)_2$ |
| 461 | $CH_3$ | 4-$OC_6H_4$-4-F | $CH_2CH=CHCl$ |
| 462 | $CH_3$ | 4-$OC_6H_4$-4-F | $CH_2CH=CCl_2$ |
| 463 | $CH_3$ | 4-$OC_6H_4$-4-F | $CH_2C(CH_3)=CH_2$ |
| 464 | $CH_3$ | 4-$OC_6H_4$-4-F | $CH_2C\equiv CH$ |
| 465 | $CH_3$ | 4-$OC_6H_4$-4-F | $CH_2Si(CH_3)_3$ |
| 466 | $CH_3$ | 4-$OC_6H_4$-4-F | $CH_2$-c.propyl-2,2-$Cl_2$ |
| 467 | $CH_3$ | 4-$OC_6H_4$-4-F | $CH_2CN$ |
| 468 | $CH_3$ | 4-$OC_6H_4$-4-F | $CH_2COOC_2H_5$ |
| 469 | $CH_3$ | 4-$OC_6H_4$-4-F | $CH(CH_3)COOC_2H_5$ |
| 470 | $CH_3$ | 4-$OC_6H_4$-4-F | $CH_2C_6H_4$-3-$CF_3$ |
| 471 | $CH_3$ | 4-$OC_6H_4$-4-F | $CH_2C_6H_4$-4-F |
| 472 | $CH_3$ | 4-$OC_6H_4$-4-F | $CH_2C_6H_4$-3-F |
| 473 | $CH_3$ | 4-$OC_6H_4$-4-F | $CH_2C_6H_4$-2-F |
| 474 | $CH_3$ | 4-$OC_6H_4$-4-F | $C(=O)OC_2H_5$ |
| 475 | $CH_3$ | 4-$OC_6H_4$-4-F | $C(=O)NHCH_3$ |
| 476 | $CH_3$ | 4-$OC_6H_4$-4-F | $C(=O)C(=O)OC_2H_5$ |
| 477 | $CH_3$ | 4-$OC_6H_4$-3-F | $CH_3$ |
| 478 | $CH_3$ | 4-$OC_6H_4$-3-F | $C_2H_5$ |
| 479 | $CH_3$ | 4-$OC_6H_4$-3-F | n-$C_3H_7$ |
| 480 | $CH_3$ | 4-$OC_6H_4$-3-F | i-$C_3H_7$ |
| 481 | $CH_3$ | 4-$OC_6H_4$-3-F | n-$C_4H_9$ |
| 482 | $CH_3$ | 4-$OC_6H_4$-3-F | n-$C_6H_{13}$ |
| 483 | $CH_3$ | 4-$OC_6H_4$-3-F | $CH_2F$ |
| 484 | $CH_3$ | 4-$OC_6H_4$-3-F | $CHF_2$ |
| 485 | $CH_3$ | 4-$OC_6H_4$-3-F | $CH_2CF_3$ |
| 486 | $CH_3$ | 4-$OC_6H_4$-3-F | $CH_2CH=CH_2$ |
| 487 | $CH_3$ | 4-$OC_6H_4$-3-F | $CH_2CH=CHCH_3$ |
| 488 | $CH_3$ | 4-$OC_6H_4$-3-F | $CH_2CH=C(CH_3)_2$ |
| 489 | $CH_3$ | 4-$OC_6H_4$-3-F | $CH_2CH=CHCl$ |
| 490 | $CH_3$ | 4-$OC_6H_4$-3-F | $CH_2CH=CCl_2$ |
| 491 | $CH_3$ | 4-$OC_6H_4$-3-F | $CH_2C(CH_3)=CH_2$ |
| 492 | $CH_3$ | 4-$OC_6H_4$-3-F | $CH_2C\equiv CH$ |
| 493 | $CH_3$ | 4-$OC_6H_4$-3-F | $CH_2Si(CH_3)_3$ |
| 494 | $CH_3$ | 4-$OC_6H_4$-3-F | $CH_2$-c.propyl-2,2-$Cl_2$ |
| 495 | $CH_3$ | 4-$OC_6H_4$-3-F | $CH_2CN$ |
| 496 | $CH_3$ | 4-$OC_6H_4$-3-F | $CH_2COOC_2H_5$ |
| 497 | $CH_3$ | 4-$OC_6H_4$-3-F | $CH(CH_3)COOC_2H_5$ |
| 498 | $CH_3$ | 4-$OC_6H_4$-3-F | $CH_2C_6H_4$-3-$CF_3$ |
| 499 | $CH_3$ | 4-$OC_6H_4$-3-F | $CH_2C_6H_4$-4-F |
| 500 | $CH_3$ | 4-$OC_6H_4$-3-F | $CH_2C_6H_4$-3-F |
| 501 | $CH_3$ | 4-$OC_6H_4$-3-F | $CH_2C_6H_4$-2-F |
| 502 | $CH_3$ | 4-$OC_6H_4$-3-F | $C(=O)OC_2H_5$ |
| 503 | $CH_3$ | 4-$OC_6H_4$-3-F | $C(=O)NHCH_3$ |
| 504 | $CH_3$ | 4-$OC_6H_4$-3-F | $C(=O)C(=O)OC_2H_5$ |
| 505 | $CH_3$ | 4-$OC_6H_4$-2-F | $CH_3$ |
| 506 | $CH_3$ | 4-$OC_6H_4$-2-F | $C_2H_5$ |
| 507 | $CH_3$ | 4-$OC_6H_4$-2-F | n-$C_3H_7$ |
| 508 | $CH_3$ | 4-$OC_6H_4$-2-F | i-$C_3H_7$ |
| 509 | $CH_3$ | 4-$OC_6H_4$-2-F | n-$C_4H_9$ |
| 510 | $CH_3$ | 4-$OC_6H_4$-2-F | n-$C_6H_{13}$ |
| 511 | $CH_3$ | 4-$OC_6H_4$-2-F | $CH_2F$ |
| 512 | $CH_3$ | 4-$OC_6H_4$-2-F | $CHF_2$ |
| 513 | $CH_3$ | 4-$OC_6H_4$-2-F | $CH_2CF_3$ |
| 514 | $CH_3$ | 4-$OC_6H_4$-2-F | $CH_2CH=CH_2$ |
| 515 | $CH_3$ | 4-$OC_6H_4$-2-F | $CH_2CH=CHCH_3$ |
| 516 | $CH_3$ | 4-$OC_6H_4$-2-F | $CH_2CH=C(CH_3)_2$ |
| 517 | $CH_3$ | 4-$OC_6H_4$-2-F | $CH_2CH=CHCl$ |
| 518 | $CH_3$ | 4-$OC_6H_4$-2-F | $CH_2CH=CCl_2$ |
| 519 | $CH_3$ | 4-$OC_6H_4$-2-F | $CH_2C(CH_3)=CH_2$ |
| 520 | $CH_3$ | 4-$OC_6H_4$-2-F | $CH_2C\equiv CH$ |
| 521 | $CH_3$ | 4-$OC_6H_4$-2-F | $CH_2Si(CH_3)_3$ |
| 522 | $CH_3$ | 4-$OC_6H_4$-2-F | $CH_2$-c.propyl-2,2-$Cl_2$ |
| 523 | $CH_3$ | 4-$OC_6H_4$-2-F | $CH_2CN$ |
| 524 | $CH_3$ | 4-$OC_6H_4$-2-F | $CH_2COOC_2H_5$ |
| 525 | $CH_3$ | 4-$OC_6H_4$-2-F | $CH(CH_3)COOC_2H_5$ |
| 526 | $CH_3$ | 4-$OC_6H_4$-2-F | $CH_2C_6H_4$-3-$CF_3$ |
| 527 | $CH_3$ | 4-$OC_6H_4$-2-F | $CH_2C_6H_4$-4-F |
| 528 | $CH_3$ | 4-$OC_6H_4$-2-F | $CH_2C_6H_4$-3-F |
| 529 | $CH_3$ | 4-$OC_6H_4$-2-F | $CH_2C_6H_4$-2-F |
| 530 | $CH_3$ | 4-$OC_6H_4$-2-F | $C(=O)OC_2H_5$ |
| 531 | $CH_3$ | 4-$OC_6H_4$-2-F | $C(=O)NHCH_3$ |
| 532 | $CH_3$ | 4-$OC_6H_4$-2-F | $C(=O)C(=O)OC_2H_5$ |
| 533 | $CH_3$ | 4-$OC_6H_4$-4-Br | $CH_3$ |
| 534 | $CH_3$ | 4-$OC_6H_4$-4-Br | $C_2H_5$ |
| 535 | $CH_3$ | 4-$OC_6H_4$-4-Br | n-$C_3H_7$ |
| 536 | $CH_3$ | 4-$OC_6H_4$-4-Br | i-$C_3H_7$ |
| 537 | $CH_3$ | 4-$OC_6H_4$-4-Br | n-$C_4H_9$ |
| 538 | $CH_3$ | 4-$OC_6H_4$-4-Br | n-$C_6H_{13}$ |
| 539 | $CH_3$ | 4-$OC_6H_4$-4-Br | $CH_2F$ |
| 540 | $CH_3$ | 4-$OC_6H_4$-4-Br | $CHF_2$ |
| 541 | $CH_3$ | 4-$OC_6H_4$-4-Br | $CH_2CF_3$ |
| 542 | $CH_3$ | 4-$OC_6H_4$-4-Br | $CH_2CH=CH_2$ |
| 543 | $CH_3$ | 4-$OC_6H_4$-4-Br | $CH_2CH=CHCH_3$ |
| 544 | $CH_3$ | 4-$OC_6H_4$-4-Br | $CH_2CH=C(CH_3)_2$ |
| 545 | $CH_3$ | 4-$OC_6H_4$-4-Br | $CH_2CH=CHCl$ |
| 546 | $CH_3$ | 4-$OC_6H_4$-4-Br | $CH_2CH=CCl_2$ |
| 547 | $CH_3$ | 4-$OC_6H_4$-4-Br | $CH_2C(CH_3)=CH_2$ |
| 548 | $CH_3$ | 4-$OC_6H_4$-4-Br | $CH_2C\equiv CH$ |
| 549 | $CH_3$ | 4-$OC_6H_4$-4-Br | $CH_2Si(CH_3)_3$ |
| 550 | $CH_3$ | 4-$OC_6H_4$-4-Br | $CH_2$-c.propyl-2,2-$Cl_2$ |
| 551 | $CH_3$ | 4-$OC_6H_4$-4-Br | $CH_2CN$ |
| 552 | $CH_3$ | 4-$OC_6H_4$-4-Br | $CH_2COOC_2H_5$ |
| 553 | $CH_3$ | 4-$OC_6H_4$-4-Br | $CH(CH_3)COOC_2H_5$ |
| 554 | $CH_3$ | 4-$OC_6H_4$-4-Br | $CH_2C_6H_4$-3-$CF_3$ |
| 555 | $CH_3$ | 4-$OC_6H_4$-4-Br | $CH_2C_6H_4$-4-F |
| 556 | $CH_3$ | 4-$OC_6H_4$-4-Br | $CH_2C_6H_4$-3-F |
| 557 | $CH_3$ | 4-$OC_6H_4$-4-Br | $CH_2C_6H_4$-2-F |
| 558 | $CH_3$ | 4-$OC_6H_4$-4-Br | $C(=O)OC_2H_5$ |
| 559 | $CH_3$ | 4-$OC_6H_4$-4-Br | $C(=O)NHCH_3$ |
| 560 | $CH_3$ | 4-$OC_6H_4$-4-Br | $C(=O)C(=O)OC_2H_5$ |
| 561 | $CH_3$ | 4-$OC_6H_4$-3-Br | $CH_3$ |
| 562 | $CH_3$ | 4-$OC_6H_4$-3-Br | $C_2H_5$ |
| 563 | $CH_3$ | 4-$OC_6H_4$-3-Br | n-$C_3H_7$ |
| 564 | $CH_3$ | 4-$OC_6H_4$-3-Br | i-$C_3H_7$ |
| 565 | $CH_3$ | 4-$OC_6H_4$-3-Br | n-$C_4H_9$ |
| 566 | $CH_3$ | 4-$OC_6H_4$-3-Br | n-$C_6H_{13}$ |
| 567 | $CH_3$ | 4-$OC_6H_4$-3-Br | $CH_2F$ |
| 568 | $CH_3$ | 4-$OC_6H_4$-3-Br | $CHF_2$ |
| 569 | $CH_3$ | 4-$OC_6H_4$-3-Br | $CH_2CF_3$ |
| 570 | $CH_3$ | 4-$OC_6H_4$-3-Br | $CH_2CH=CH_2$ |
| 571 | $CH_3$ | 4-$OC_6H_4$-3-Br | $CH_2CH=CHCH_3$ |
| 572 | $CH_3$ | 4-$OC_6H_4$-3-Br | $CH_2CH=C(CH_3)_2$ |
| 573 | $CH_3$ | 4-$OC_6H_4$-3-Br | $CH_2CH=CHCl$ |
| 574 | $CH_3$ | 4-$OC_6H_4$-3-Br | $CH_2CH=CCl_2$ |
| 575 | $CH_3$ | 4-$OC_6H_4$-3-Br | $CH_2C(CH_3)=CH_2$ |
| 576 | $CH_3$ | 4-$OC_6H_4$-3-Br | $CH_2C\equiv CH$ |
| 577 | $CH_3$ | 4-$OC_6H_4$-3-Br | $CH_2Si(CH_3)_3$ |
| 578 | $CH_3$ | 4-$OC_6H_4$-3-Br | $CH_2$-c.propyl-2,2-$Cl_2$ |
| 579 | $CH_3$ | 4-$OC_6H_4$-3-Br | $CH_2CN$ |
| 580 | $CH_3$ | 4-$OC_6H_4$-3-Br | $CH_2COOC_2H_5$ |
| 581 | $CH_3$ | 4-$OC_6H_4$-3-Br | $CH(CH_3)COOC_2H_5$ |
| 582 | $CH_3$ | 4-$OC_6H_4$-3-Br | $CH_2C_6H_4$-3-$CF_3$ |
| 583 | $CH_3$ | 4-$OC_6H_4$-3-Br | $CH_2C_6H_4$-4-F |
| 584 | $CH_3$ | 4-$OC_6H_4$-3-Br | $CH_2C_6H_4$-3-F |
| 585 | $CH_3$ | 4-$OC_6H_4$-3-Br | $CH_2C_6H_4$-2-F |
| 586 | $CH_3$ | 4-$OC_6H_4$-3-Br | $C(=O)OC_2H_5$ |
| 587 | $CH_3$ | 4-$OC_6H_4$-3-Br | $C(=O)NHCH_3$ |
| 588 | $CH_3$ | 4-$OC_6H_4$-3-Br | $C(=O)C(=O)OC_2H_5$ |
| 589 | $CH_3$ | 4-$OC_6H_4$-2-Br | $CH_3$ |

TABLE A-continued

| Compound No. | R$_2$ | (R$_5$)$_n$ | A-R$_7$ |
|---|---|---|---|
| 590 | CH$_3$ | 4-OC$_6$H$_4$-2-Br | C$_2$H$_5$ |
| 591 | CH$_3$ | 4-OC$_6$H$_4$-2-Br | n-C$_3$H$_7$ |
| 592 | CH$_3$ | 4-OC$_6$H$_4$-2-Br | i-C$_3$H$_7$ |
| 593 | CH$_3$ | 4-OC$_6$H$_4$-2-Br | n-C$_4$H$_9$ |
| 594 | CH$_3$ | 4-OC$_6$H$_4$-2-Br | n-C$_6$H$_{13}$ |
| 595 | CH$_3$ | 4-OC$_6$H$_4$-2-Br | CH$_2$F |
| 596 | CH$_3$ | 4-OC$_6$H$_4$-2-Br | CHF$_2$ |
| 597 | CH$_3$ | 4-OC$_6$H$_4$-2-Br | CH$_2$CF$_3$ |
| 598 | CH$_3$ | 4-OC$_6$H$_4$-2-Br | CH$_2$CH=CH$_2$ |
| 599 | CH$_3$ | 4-OC$_6$H$_4$-2-Br | CH$_2$CH=CHCH$_3$ |
| 600 | CH$_3$ | 4-OC$_6$H$_4$-2-Br | CH$_2$CH=C(CH$_3$)$_2$ |
| 601 | CH$_3$ | 4-OC$_6$H$_4$-2-Br | CH$_2$CH=CHCl |
| 602 | CH$_3$ | 4-OC$_6$H$_4$-2-Br | CH$_2$CH=CCl$_2$ |
| 603 | CH$_3$ | 4-OC$_6$H$_4$-2-Br | CH$_2$C(CH$_3$)=CH$_2$ |
| 604 | CH$_3$ | 4-OC$_6$H$_4$-2-Br | CH$_2$C=CH |
| 605 | CH$_3$ | 4-OC$_6$H$_4$-2-Br | CH$_2$Si(CH$_3$)$_3$ |
| 606 | CH$_3$ | 4-OC$_6$H$_4$-2-Br | CH$_2$-c.propyl-2,2-Cl$_2$ |
| 607 | CH$_3$ | 4-OC$_6$H$_4$-2-Br | CH$_2$CN |
| 608 | CH$_3$ | 4-OC$_6$H$_4$-2-Br | CH$_2$COOC$_2$H$_5$ |
| 609 | CH$_3$ | 4-OC$_6$H$_4$-2-Br | CH(CH$_3$)COOC$_2$H$_5$ |
| 610 | CH$_3$ | 4-OC$_6$H$_4$-2-Br | CH$_2$C$_6$H$_4$-3-CF$_3$ |
| 611 | CH$_3$ | 4-OC$_6$H$_4$-2-Br | CH$_2$C$_6$H$_4$-4-F |
| 612 | CH$_3$ | 4-OC$_6$H$_4$-2-Br | CH$_2$C$_6$H$_4$-3-F |
| 613 | CH$_3$ | 4-OC$_6$H$_4$-2-Br | CH$_2$C$_6$H$_4$-2-F |
| 614 | CH$_3$ | 4-OC$_6$H$_4$-2-Br | C(=O)OC$_2$H$_5$ |
| 615 | CH$_3$ | 4-OC$_6$H$_4$-2-Br | C(=O)NHCH$_3$ |
| 616 | CH$_3$ | 4-OC$_6$H$_4$-2-Br | C(=O)C(=O)OC$_2$H$_5$ |
| 617 | CH$_3$ | 4-OC$_6$H$_3$-2,4-Cl$_2$ | CH$_3$ |
| 618 | CH$_3$ | 4-OC$_6$H$_3$-2,4-Cl$_2$ | C$_2$H$_5$ |
| 619 | CH$_3$ | 4-OC$_6$H$_3$-2,4-Cl$_2$ | n-C$_3$H$_7$ |
| 620 | CH$_3$ | 4-OC$_6$H$_3$-2,4-Cl$_2$ | i-C$_3$H$_7$ |
| 621 | CH$_3$ | 4-OC$_6$H$_3$-2,4-Cl$_2$ | n-C$_4$H$_9$ |
| 622 | CH$_3$ | 4-OC$_6$H$_3$-2,4-Cl$_2$ | n-C$_6$H$_{13}$ |
| 623 | CH$_3$ | 4-OC$_6$H$_3$-2,4-Cl$_2$ | CH$_2$F |
| 624 | CH$_3$ | 4-OC$_6$H$_3$-2,4-Cl$_2$ | CHF$_2$ |
| 625 | CH$_3$ | 4-OC$_6$H$_3$-2,4-Cl$_2$ | CH$_2$CF$_3$ |
| 626 | CH$_3$ | 4-OC$_6$H$_3$-2,4-Cl$_2$ | CH$_2$CH=CH$_2$ |
| 627 | CH$_3$ | 4-OC$_6$H$_3$-2,4-Cl$_2$ | CH$_2$CH=CHCH$_3$ |
| 628 | CH$_3$ | 4-OC$_6$H$_3$-2,4-Cl$_2$ | CH$_2$CH=C(CH$_3$)$_2$ |
| 629 | CH$_3$ | 4-OC$_6$H$_3$-2,4-Cl$_2$ | CH$_2$CH=CHCl |
| 630 | CH$_3$ | 4-OC$_6$H$_3$-2,4-Cl$_2$ | CH$_2$CH=CCl$_2$ |
| 631 | CH$_3$ | 4-OC$_6$H$_3$-2,4-Cl$_2$ | CH$_2$C(CH$_3$)=CH$_2$ |
| 632 | CH$_3$ | 4-OC$_6$H$_3$-2,4-Cl$_2$ | CH$_2$C=CH |
| 633 | CH$_3$ | 4-OC$_6$H$_3$-2,4-Cl$_2$ | CH$_2$Si(CH$_3$)$_3$ |
| 634 | CH$_3$ | 4-OC$_6$H$_3$-2,4-Cl$_2$ | CH$_2$-c.propyl-2,2-Cl$_2$ |
| 635 | CH$_3$ | 4-OC$_6$H$_3$-2,4-Cl$_2$ | CH$_2$CN |
| 636 | CH$_3$ | 4-OC$_6$H$_3$-2,4-Cl$_2$ | CH$_2$COOC$_2$H$_5$ |
| 637 | CH$_3$ | 4-OC$_6$H$_3$-2,4-Cl$_2$ | CH(CH$_3$)COOC$_2$H$_5$ |
| 638 | CH$_3$ | 4-OC$_6$H$_3$-2,4-Cl$_2$ | CH$_2$C$_6$H$_4$-3-CF$_3$ |
| 639 | CH$_3$ | 4-OC$_6$H$_3$-2,4-Cl$_2$ | CH$_2$C$_6$H$_4$-4-F |
| 640 | CH$_3$ | 4-OC$_6$H$_3$-2,4-Cl$_2$ | CH$_2$C$_6$H$_4$-3-F |
| 641 | CH$_3$ | 4-OC$_6$H$_3$-2,4-Cl$_2$ | CH$_2$C$_6$H$_4$-2-F |
| 642 | CH$_3$ | 4-OC$_6$H$_3$-2,4-Cl$_2$ | C(=O)OC$_2$H$_5$ |
| 643 | CH$_3$ | 4-OC$_6$H$_3$-2,4-Cl$_2$ | C(=O)NHCH$_3$ |
| 644 | CH$_3$ | 4-OC$_6$H$_3$-2,4-Cl$_2$ | C(=O)C(=O)OC$_2$H$_5$ |
| 645 | CH$_3$ | 4-OC$_6$H$_3$-3,4-Cl$_2$ | CH$_3$ |
| 646 | CH$_3$ | 4-OC$_6$H$_3$-3,4-Cl$_2$ | C$_2$H$_5$ |
| 647 | CH$_3$ | 4-OC$_6$H$_3$-3,4-Cl$_2$ | n-C$_3$H$_7$ |
| 648 | CH$_3$ | 4-OC$_6$H$_3$-3,4-Cl$_2$ | i-C$_3$H$_7$ |
| 649 | CH$_3$ | 4-OC$_6$H$_3$-3,4-Cl$_2$ | n-C$_4$H$_9$ |
| 650 | CH$_3$ | 4-OC$_6$H$_3$-3,4-Cl$_2$ | n-C$_6$H$_{13}$ |
| 651 | CH$_3$ | 4-OC$_6$H$_3$-3,4-Cl$_2$ | CH$_2$F |
| 652 | CH$_3$ | 4-OC$_6$H$_3$-3,4-Cl$_2$ | CHF$_2$ |
| 653 | CH$_3$ | 4-OC$_6$H$_3$-3,4-Cl$_2$ | CH$_2$CF$_3$ |
| 654 | CH$_3$ | 4-OC$_6$H$_3$-3,4-Cl$_2$ | CH$_2$CH=CH$_2$ |
| 655 | CH$_3$ | 4-OC$_6$H$_3$-3,4-Cl$_2$ | CH$_2$CH=CHCH$_3$ |
| 656 | CH$_3$ | 4-OC$_6$H$_3$-3,4-Cl$_2$ | CH$_2$CH=C(CH$_3$)$_2$ |
| 657 | CH$_3$ | 4-OC$_6$H$_3$-3,4-Cl$_2$ | CH$_2$CH=CHCl |
| 658 | CH$_3$ | 4-OC$_6$H$_3$-3,4-Cl$_2$ | CH$_2$CH=CCl$_2$ |
| 659 | CH$_3$ | 4-OC$_6$H$_3$-3,4-Cl$_2$ | CH$_2$C(CH$_3$)=CH$_2$ |
| 660 | CH$_3$ | 4-OC$_6$H$_3$-3,4-Cl$_2$ | CH$_2$C=CH |
| 661 | CH$_3$ | 4-OC$_6$H$_3$-3,4-Cl$_2$ | CH$_2$Si(CH$_3$)$_3$ |
| 662 | CH$_3$ | 4-OC$_6$H$_3$-3,4-Cl$_2$ | CH$_2$-c.propyl-2,2-Cl$_2$ |
| 663 | CH$_3$ | 4-OC$_6$H$_3$-3,4-Cl$_2$ | CH$_2$CN |
| 664 | CH$_3$ | 4-OC$_6$H$_3$-3,4-Cl$_2$ | CH$_2$COOC$_2$H$_5$ |
| 665 | CH$_3$ | 4-OC$_6$H$_3$-3,4-Cl$_2$ | CH(CH$_3$)COOC$_2$H$_5$ |
| 666 | CH$_3$ | 4-OC$_6$H$_3$-3,4-Cl$_2$ | CH$_2$C$_6$H$_4$-3-CF$_3$ |
| 667 | CH$_3$ | 4-OC$_6$H$_3$-3,4-Cl$_2$ | CH$_2$C$_6$H$_4$-4-F |
| 668 | CH$_3$ | 4-OC$_6$H$_3$-3,4-Cl$_2$ | CH$_2$C$_6$H$_4$-3-F |
| 669 | CH$_3$ | 4-OC$_6$H$_3$-3,4-Cl$_2$ | CH$_2$C$_6$H$_4$-2-F |
| 670 | CH$_3$ | 4-OC$_6$H$_3$-3,4-Cl$_2$ | C(=O)OC$_2$H$_5$ |
| 671 | CH$_3$ | 4-OC$_6$H$_3$-3,4-Cl$_2$ | C(=O)NHCH$_3$ |
| 672 | CH$_3$ | 4-OC$_6$H$_3$-3,4-Cl$_2$ | C(=O)C(=O)OC$_2$H$_5$ |
| 673 | CH$_3$ | 4-OC$_6$H$_3$-2-Cl,4-Br | CH$_3$ |
| 674 | CH$_3$ | 4-OC$_6$H$_3$-2-Cl,4-Br | C$_2$H$_5$ |
| 675 | CH$_3$ | 4-OC$_6$H$_3$-2-Cl,4-Br | n-C$_3$H$_7$ |
| 676 | CH$_3$ | 4-OC$_6$H$_3$-2-Cl,4-Br | i-C$_3$H$_7$ |
| 677 | CH$_3$ | 4-OC$_6$H$_3$-2-Cl,4-Br | n-C$_4$H$_9$ |
| 678 | CH$_3$ | 4-OC$_6$H$_3$-2-Cl,4-Br | n-C$_6$H$_{13}$ |
| 679 | CH$_3$ | 4-OC$_6$H$_3$-2-Cl,4-Br | CH$_2$F |
| 680 | CH$_3$ | 4-OC$_6$H$_3$-2-Cl,4-Br | CHF$_2$ |
| 681 | CH$_3$ | 4-OC$_6$H$_3$-2-Cl,4-Br | CH$_2$CF$_3$ |
| 682 | CH$_3$ | 4-OC$_6$H$_3$-2-Cl,4-Br | CH$_2$CH=CH$_2$ |
| 683 | CH$_3$ | 4-OC$_6$H$_3$-2-Cl,4-Br | CH$_2$CH=CHCH$_3$ |
| 684 | CH$_3$ | 4-OC$_6$H$_3$-2-Cl,4-Br | CH$_2$CH=C(CH$_3$)$_2$ |
| 685 | CH$_3$ | 4-OC$_6$H$_3$-2-Cl,4-Br | CH$_2$CH=CHCl |
| 686 | CH$_3$ | 4-OC$_6$H$_3$-2-Cl,4-Br | CH$_2$CH=CCl$_2$ |
| 687 | CH$_3$ | 4-OC$_6$H$_3$-2-Cl,4-Br | CH$_2$C(CH$_3$)=CH$_2$ |
| 688 | CH$_3$ | 4-OC$_6$H$_3$-2-Cl,4-Br | CH$_2$C=CH |
| 689 | CH$_3$ | 4-OC$_6$H$_3$-2-Cl,4-Br | CH$_2$Si(CH$_3$)$_3$ |
| 690 | CH$_3$ | 4-OC$_6$H$_3$-2-Cl,4-Br | CH$_2$-c.propyl-2,2-Cl$_2$ |
| 691 | CH$_3$ | 4-OC$_6$H$_3$-2-Cl,4-Br | CH$_2$CN |
| 692 | CH$_3$ | 4-OC$_6$H$_3$-2-Cl,4-Br | CH$_2$COOC$_2$H$_5$ |
| 693 | CH$_3$ | 4-OC$_6$H$_3$-2-Cl,4-Br | CH(CH$_3$)COOC$_2$H$_5$ |
| 694 | CH$_3$ | 4-OC$_6$H$_3$-2-Cl,4-Br | CH$_2$C$_6$H$_4$-3-CF$_3$ |
| 695 | CH$_3$ | 4-OC$_6$H$_3$-2-Cl,4-Br | CH$_2$C$_6$H$_4$-4-F |
| 696 | CH$_3$ | 4-OC$_6$H$_3$-2-Cl,4-Br | CH$_2$C$_6$H$_4$-3-F |
| 697 | CH$_3$ | 4-OC$_6$H$_3$-2-Cl,4-Br | CH$_2$C$_6$H$_4$-2-F |
| 698 | CH$_3$ | 4-OC$_6$H$_3$-2-Cl,4-Br | C(=O)OC$_2$H$_5$ |
| 699 | CH$_3$ | 4-OC$_6$H$_3$-2-Cl,4-Br | C(=O)NHCH$_3$ |
| 700 | CH$_3$ | 4-OC$_6$H$_3$-2-Cl,4-Br | C(=O)C(=O)OC$_2$H$_5$ |
| 701 | CH$_3$ | 4-OC$_6$H$_3$-3,4-(-CH$_2$O-) | CH$_3$ |
| 702 | CH$_3$ | 4-OC$_6$H$_3$-3,4-(-CH$_2$O-) | C$_2$H$_5$ |
| 703 | CH$_3$ | 4-OC$_6$H$_3$-3,4-(-CH$_2$O-) | n-C$_3$H$_7$ |
| 704 | CH$_3$ | 4-OC$_6$H$_3$-3,4-(-CH$_2$O-) | i-C$_3$H$_7$ |
| 705 | CH$_3$ | 4-OC$_6$H$_3$-3,4-(-CH$_2$O-) | n-C$_4$H$_9$ |
| 706 | CH$_3$ | 4-OC$_6$H$_3$-3,4-(-CH$_2$O-) | n-C$_6$H$_{13}$ |
| 707 | CH$_3$ | 4-OC$_6$H$_3$-3,4-(-CH$_2$O-) | CH$_2$F |
| 708 | CH$_3$ | 4-OC$_6$H$_3$-3,4-(-CH$_2$O-) | CHF$_2$ |
| 709 | CH$_3$ | 4-OC$_6$H$_3$-3,4-(-CH$_2$O-) | CH$_2$CF$_3$ |
| 710 | CH$_3$ | 4-OC$_6$H$_3$-3,4-(-CH$_2$O-) | CH$_2$CH=CH$_2$ |
| 711 | CH$_3$ | 4-OC$_6$H$_3$-3,4-(-CH$_2$O-) | CH$_2$CH=CHCH$_3$ |
| 712 | CH$_3$ | 4-OC$_6$H$_3$-3,4-(-CH$_2$O-) | CH$_2$CH=C(CH$_3$)$_2$ |
| 713 | CH$_3$ | 4-OC$_6$H$_3$-3,4-(-CH$_2$O-) | CH$_2$CH=CHCl |
| 714 | CH$_3$ | 4-OC$_6$H$_3$-3,4-(-CH$_2$O-) | CH$_2$CH=CCl$_2$ |
| 715 | CH$_3$ | 4-OC$_6$H$_3$-3,4-(-CH$_2$O-) | CH$_2$C(CH$_3$)=CH$_2$ |
| 716 | CH$_3$ | 4-OC$_6$H$_3$-3,4-(-CH$_2$O-) | CH$_2$C=CH |
| 717 | CH$_3$ | 4-OC$_6$H$_3$-3,4-(-CH$_2$O-) | CH$_2$Si(CH$_3$)$_3$ |
| 718 | CH$_3$ | 4-OC$_6$H$_3$-3,4-(-CH$_2$O-) | CH$_2$-c.propyl-2,2-Cl$_2$ |
| 719 | CH$_3$ | 4-OC$_6$H$_3$-3,4-(-CH$_2$O-) | CH$_2$CN |
| 720 | CH$_3$ | 4-OC$_6$H$_3$-3,4-(-CH$_2$O-) | CH$_2$COOC$_2$H$_5$ |
| 721 | CH$_3$ | 4-OC$_6$H$_3$-3,4-(-CH$_2$O-) | CH(CH$_3$)COOC$_2$H$_5$ |
| 722 | CH$_3$ | 4-OC$_6$H$_3$-3,4-(-CH$_2$O-) | CH$_2$C$_6$H$_4$-3-CF$_3$ |
| 723 | CH$_3$ | 4-OC$_6$H$_3$-3,4-(-CH$_2$O-) | CH$_2$C$_6$H$_4$-4-F |
| 724 | CH$_3$ | 4-OC$_6$H$_3$-3,4-(-CH$_2$O-) | CH$_2$C$_6$H$_4$-3-F |
| 725 | CH$_3$ | 4-OC$_6$H$_3$-3,4-(-CH$_2$O-) | CH$_2$C$_6$H$_4$-2-F |
| 726 | CH$_3$ | 4-OC$_6$H$_3$-3,4-(-CH$_2$O-) | C(=O)OC$_2$H$_5$ |
| 727 | CH$_3$ | 4-OC$_6$H$_3$-3,4-(-CH$_2$O-) | C(=O)NHCH$_3$ |
| 728 | CH$_3$ | 4-OC$_6$H$_3$-3,4-(-CH$_2$O-) | C(=O)C(=O)OC$_2$H$_5$ |
| 729 | CH$_3$ | 4-OC$_6$H$_4$-4-SCH$_3$ | CH$_3$ |
| 730 | CH$_3$ | 4-OC$_6$H$_4$-4-SCH$_3$ | C$_2$H$_5$ |
| 731 | CH$_3$ | 4-OC$_6$H$_4$-4-SCH$_3$ | n-C$_3$H$_7$ |
| 732 | CH$_3$ | 4-OC$_6$H$_4$-4-SCH$_3$ | i-C$_3$H$_7$ |
| 733 | CH$_3$ | 4-OC$_6$H$_4$-4-SCH$_3$ | n-C$_4$H$_9$ |
| 734 | CH$_3$ | 4-OC$_6$H$_4$-4-SCH$_3$ | n-C$_6$H$_{13}$ |
| 735 | CH$_3$ | 4-OC$_6$H$_4$-4-SCH$_3$ | CH$_2$F |
| 736 | CH$_3$ | 4-OC$_6$H$_4$-4-SCH$_3$ | CHF$_2$ |
| 737 | CH$_3$ | 4-OC$_6$H$_4$-4-SCH$_3$ | CH$_2$CF$_3$ |
| 738 | CH$_3$ | 4-OC$_6$H$_4$-4-SCH$_3$ | CH$_2$CH=CH$_2$ |
| 739 | CH$_3$ | 4-OC$_6$H$_4$-4-SCH$_3$ | CH$_2$CH=CHCH$_3$ |
| 740 | CH$_3$ | 4-OC$_6$H$_4$-4-SCH$_3$ | CH$_2$CH=C(CH$_3$)$_2$ |
| 741 | CH$_3$ | 4-OC$_6$H$_4$-4-SCH$_3$ | CH$_2$CH=CHCl |

TABLE A-continued

| Compound No. | R₂ | (R₅)ₙ | A-R₇ |
|---|---|---|---|
| 742 | CH₃ | 4-OC₆H₄-4-SCH₃ | CH₂CH=CCl₂ |
| 743 | CH₃ | 4-OC₆H₄-4-SCH₃ | CH₂C(CH₃)=CH₂ |
| 744 | CH₃ | 4-OC₆H₄-4-SCH₃ | CH₂C=CH |
| 745 | CH₃ | 4-OC₆H₄-4-SCH₃ | CH₂Si(CH₃)₃ |
| 746 | CH₃ | 4-OC₆H₄-4-SCH₃ | CH₂-c.propyl-2,2-Cl₂ |
| 747 | CH₃ | 4-OC₆H₄-4-SCH₃ | CH₂CN |
| 748 | CH₃ | 4-OC₆H₄-4-SCH₃ | CH₂COOC₂H₅ |
| 749 | CH₃ | 4-OC₆H₄-4-SCH₃ | CH(CH₃)COOC₂H₅ |
| 750 | CH₃ | 4-OC₆H₄-4-SCH₃ | CH₂C₆H₄-3-CF₃ |
| 751 | CH₃ | 4-OC₆H₄-4-SCH₃ | CH₂C₆H₄-4-F |
| 752 | CH₃ | 4-OC₆H₄-4-SCH₃ | CH₂C₆H₄-3-F |
| 753 | CH₃ | 4-OC₆H₄-4-SCH₃ | CH₂C₆H₄-2-F |
| 754 | CH₃ | 4-OC₆H₄-4-SCH₃ | C(=O)OC₂H₅ |
| 755 | CH₃ | 4-OC₆H₄-4-SCH₃ | C(=O)NHCH₃ |
| 756 | CH₃ | 4-OC₆H₄-4-SCH₃ | C(=O)C(=O)OC₂H₅ |
| 757 | CH₃ | 4-OC₆H₄-4-OCH₃ | CH₃ |
| 758 | CH₃ | 4-OC₆H₄-4-OCH₃ | C₂H₅ |
| 759 | CH₃ | 4-OC₆H₄-4-OCH₃ | n-C₃H₇ |
| 760 | CH₃ | 4-OC₆H₄-4-OCH₃ | i-C₃H₇ |
| 761 | CH₃ | 4-OC₆H₄-4-OCH₃ | n-C₄H₉ |
| 762 | CH₃ | 4-OC₆H₄-4-OCH₃ | n-C₆H₁₃ |
| 763 | CH₃ | 4-OC₆H₄-4-OCH₃ | CH₂F |
| 764 | CH₃ | 4-OC₆H₄-4-OCH₃ | CHF₂ |
| 765 | CH₃ | 4-OC₆H₄-4-OCH₃ | CH₂CF₃ |
| 766 | CH₃ | 4-OC₆H₄-4-OCH₃ | CH₂CH=CH₂ |
| 767 | CH₃ | 4-OC₆H₄-4-OCH₃ | CH₂CH=CHCH₃ |
| 768 | CH₃ | 4-OC₆H₄-4-OCH₃ | CH₂CH=C(CH₃)₂ |
| 769 | CH₃ | 4-OC₆H₄-4-OCH₃ | CH₂CH=CHCl |
| 770 | CH₃ | 4-OC₆H₄-4-OCH₃ | CH₂CH=CCl₂ |
| 771 | CH₃ | 4-OC₆H₄-4-OCH₃ | CH₂C(CH₃)=CH₂ |
| 772 | CH₃ | 4-OC₆H₄-4-OCH₃ | CH₂C=CH |
| 773 | CH₃ | 4-OC₆H₄-4-OCH₃ | CH₂Si(CH₃)₃ |
| 774 | CH₃ | 4-OC₆H₄-4-OCH₃ | CH₂-c.propyl-2,2-Cl₂ |
| 775 | CH₃ | 4-OC₆H₄-4-OCH₃ | CH₂CN |
| 776 | CH₃ | 4-OC₆H₄-4-OCH₃ | CH₂COOC₂H₅ |
| 777 | CH₃ | 4-OC₆H₄-4-OCH₃ | CH(CH₃)COOC₂H₅ |
| 778 | CH₃ | 4-OC₆H₄-4-OCH₃ | CH₂C₆H₄-3-CF₃ |
| 779 | CH₃ | 4-OC₆H₄-4-OCH₃ | CH₂C₆H₄-4-F |
| 780 | CH₃ | 4-OC₆H₄-4-OCH₃ | CH₂C₆H₄-3-F |
| 781 | CH₃ | 4-OC₆H₄-4-OCH₃ | CH₂C₆H₄-2-F |
| 782 | CH₃ | 4-OC₆H₄-4-OCH₃ | C(=O)OC₂H₅ |
| 783 | CH₃ | 4-OC₆H₄-4-OCH₃ | C(=O)NHCH₃ |
| 784 | CH₃ | 4-OC₆H₄-4-OCH₃ | C(=O)C(=O)OC₂H₅ |
| 785 | CH₃ | 4-OC₆H₄-4-t-butyl | CH₃ |
| 786 | CH₃ | 4-OC₆H₄-4-t-butyl | C₂H₅ |
| 787 | CH₃ | 4-OC₆H₄-4-t-butyl | n-C₃H₇ |
| 788 | CH₃ | 4-OC₆H₄-4-t-butyl | i-C₃H₇ |
| 789 | CH₃ | 4-OC₆H₄-4-t-butyl | n-C₄H₉ |
| 790 | CH₃ | 4-OC₆H₄-4-t-butyl | n-C₆H₁₃ |
| 791 | CH₃ | 4-OC₆H₄-4-t-butyl | CH₂F |
| 792 | CH₃ | 4-OC₆H₄-4-t-butyl | CHF₂ |
| 793 | CH₃ | 4-OC₆H₄-4-t-butyl | CH₂CF₃ |
| 794 | CH₃ | 4-OC₆H₄-4-t-butyl | CH₂CH=CH₂ |
| 795 | CH₃ | 4-OC₆H₄-4-t-butyl | CH₂CH=CHCH₃ |
| 796 | CH₃ | 4-OC₆H₄-4-t-butyl | CH₂CH=C(CH₃)₂ |
| 797 | CH₃ | 4-OC₆H₄-4-t-butyl | CH₂CH=CHCl |
| 798 | CH₃ | 4-OC₆H₄-4-t-butyl | CH₂CH=CCl₂ |
| 799 | CH₃ | 4-OC₆H₄-4-t-butyl | CH₂C(CH₃)=CH₂ |
| 800 | CH₃ | 4-OC₆H₄-4-t-butyl | CH₂C=CH |
| 801 | CH₃ | 4-OC₆H₄-4-t-butyl | CH₂Si(CH₃)₃ |
| 802 | CH₃ | 4-OC₆H₄-4-t-butyl | CH₂-c.propyl-2,2-Cl₂ |
| 803 | CH₃ | 4-OC₆H₄-4-t-butyl | CH₂CN |
| 804 | CH₃ | 4-OC₆H₄-4-t-butyl | CH₂COOC₂H₅ |
| 805 | CH₃ | 4-OC₆H₄-4-t-butyl | CH(CH₃)COOC₂H₅ |
| 806 | CH₃ | 4-OC₆H₄-4-t-butyl | CH₂C₆H₄-3-CF₃ |
| 807 | CH₃ | 4-OC₆H₄-4-t-butyl | CH₂C₆H₄-4-F |
| 808 | CH₃ | 4-OC₆H₄-4-t-butyl | CH₂C₆H₄-3-F |
| 809 | CH₃ | 4-OC₆H₄-4-t-butyl | CH₂C₆H₄-2-F |
| 810 | CH₃ | 4-OC₆H₄-4-t-butyl | C(=O)OC₂H₅ |
| 811 | CH₃ | 4-OC₆H₄-4-t-butyl | C(=O)NHCH₃ |
| 812 | CH₃ | 4-OC₆H₄-4-t-butyl | C(=O)C(=O)OC₂H₅ |
| 813 | CH₃ | 4-OC₆H₄-4-CF₃ | CH₃ |
| 814 | CH₃ | 4-OC₆H₄-4-CF₃ | C₂H₅ |
| 815 | CH₃ | 4-OC₆H₄-4-CF₃ | n-C₃H₇ |
| 816 | CH₃ | 4-OC₆H₄-4-CF₃ | i-C₃H₇ |
| 817 | CH₃ | 4-OC₆H₄-4-CF₃ | n-C₄H₉ |
| 818 | CH₃ | 4-OC₆H₄-4-CF₃ | n-C₆H₁₃ |
| 819 | CH₃ | 4-OC₆H₄-4-CF₃ | CH₂F |
| 820 | CH₃ | 4-OC₆H₄-4-CF₃ | CHF₂ |
| 821 | CH₃ | 4-OC₆H₄-4-CF₃ | CH₂CF₃ |
| 822 | CH₃ | 4-OC₆H₄-4-CF₃ | CH₂CH=CH₂ |
| 823 | CH₃ | 4-OC₆H₄-4-CF₃ | CH₂CH=CHCH₃ |
| 824 | CH₃ | 4-OC₆H₄-4-CF₃ | CH₂CH=C(CH₃)₂ |
| 825 | CH₃ | 4-OC₆H₄-4-CF₃ | CH₂CH=CHCl |
| 826 | CH₃ | 4-OC₆H₄-4-CF₃ | CH₂CH=CCl₂ |
| 827 | CH₃ | 4-OC₆H₄-4-CF₃ | CH₂C(CH₃)=CH₂ |
| 828 | CH₃ | 4-OC₆H₄-4-CF₃ | CH₂C=CH |
| 829 | CH₃ | 4-OC₆H₄-4-CF₃ | CH₂Si(CH₃)₃ |
| 830 | CH₃ | 4-OC₆H₄-4-CF₃ | CH₂-c.propyl-2,2-Cl₂ |
| 831 | CH₃ | 4-OC₆H₄-4-CF₃ | CH₂CN |
| 832 | CH₃ | 4-OC₆H₄-4-CF₃ | CH₂COOC₂H₅ |
| 833 | CH₃ | 4-OC₆H₄-4-CF₃ | CH(CH₃)COOC₂H₅ |
| 834 | CH₃ | 4-OC₆H₄-4-CF₃ | CH₂C₆H₄-3-CF₃ |
| 835 | CH₃ | 4-OC₆H₄-4-CF₃ | CH₂C₆H₄-4-F |
| 836 | CH₃ | 4-OC₆H₄-4-CF₃ | CH₂C₆H₄-3-F |
| 837 | CH₃ | 4-OC₆H₄-4-CF₃ | CH₂C₆H₄-2-F |
| 838 | CH₃ | 4-OC₆H₄-4-CF₃ | C(=O)OC₂H₅ |
| 839 | CH₃ | 4-OC₆H₄-4-CF₃ | C(=O)NHCH₃ |
| 840 | CH₃ | 4-OC₆H₄-4-CF₃ | C(=O)C(=O)OC₂H₅ |
| 841 | CH₃ | 4-OC₆H₄-2-CF₃ | CH₃ |
| 842 | CH₃ | 4-OC₆H₄-2-CF₃ | C₂H₅ |
| 843 | CH₃ | 4-OC₆H₄-2-CF₃ | n-C₃H₇ |
| 844 | CH₃ | 4-OC₆H₄-2-CF₃ | i-C₃H₇ |
| 845 | CH₃ | 4-OC₆H₄-2-CF₃ | n-C₄H₉ |
| 846 | CH₃ | 4-OC₆H₄-2-CF₃ | n-C₆H₁₃ |
| 847 | CH₃ | 4-OC₆H₄-2-CF₃ | CH₂F |
| 848 | CH₃ | 4-OC₆H₄-2-CF₃ | CHF₂ |
| 849 | CH₃ | 4-OC₆H₄-2-CF₃ | CH₂CF₃ |
| 850 | CH₃ | 4-OC₆H₄-2-CF₃ | CH₂CH=CH₂ |
| 851 | CH₃ | 4-OC₆H₄-2-CF₃ | CH₂CH=CHCH₃ |
| 852 | CH₃ | 4-OC₆H₄-2-CF₃ | CH₂CH=C(CH₃)₂ |
| 853 | CH₃ | 4-OC₆H₄-2-CF₃ | CH₂CH=CHCl |
| 854 | CH₃ | 4-OC₆H₄-2-CF₃ | CH₂CH=CCl₂ |
| 855 | CH₃ | 4-OC₆H₄-2-CF₃ | CH₂C(CH₃)=CH₂ |
| 856 | CH₃ | 4-OC₆H₄-2-CF₃ | CH₂C=CH |
| 857 | CH₃ | 4-OC₆H₄-2-CF₃ | CH₂Si(CH₃)₃ |
| 858 | CH₃ | 4-OC₆H₄-2-CF₃ | CH₂-c.propyl-2,2-Cl₂ |
| 859 | CH₃ | 4-OC₆H₄-2-CF₃ | CH₂CN |
| 860 | CH₃ | 4-OC₆H₄-2-CF₃ | CH₂COOC₂H₅ |
| 861 | CH₃ | 4-OC₆H₄-2-CF₃ | CH(CH₃)COOC₂H₅ |
| 862 | CH₃ | 4-OC₆H₄-2-CF₃ | CH₂C₆H₄-3-CF₃ |
| 863 | CH₃ | 4-OC₆H₄-2-CF₃ | CH₂C₆H₄-4-F |
| 864 | CH₃ | 4-OC₆H₄-2-CF₃ | CH₂C₆H₄-3-F |
| 865 | CH₃ | 4-OC₆H₄-2-CF₃ | CH₂C₆H₄-2-F |
| 866 | CH₃ | 4-OC₆H₄-2-CF₃ | C(=O)OC₂H₅ |
| 867 | CH₃ | 4-OC₆H₄-2-CF₃ | C(=O)NHCH₃ |
| 868 | CH₃ | 4-OC₆H₄-2-CF₃ | C(=O)C(=O)OC₂H₅ |
| 869 | CH₃ | 4-OCH₂C₆H₄-4-Cl | CH₃ |
| 870 | CH₃ | 4-OCH₂C₆H₄-4-Cl | C₂H₅ |
| 871 | CH₃ | 4-OCH₂C₆H₄-4-Cl | n-C₃H₇ |
| 872 | CH₃ | 4-OCH₂C₆H₄-4-Cl | i-C₃H₇ |
| 873 | CH₃ | 4-OCH₂C₆H₄-4-Cl | n-C₄H₉ |
| 874 | CH₃ | 4-OCH₂C₆H₄-4-Cl | n-C₆H₁₃ |
| 875 | CH₃ | 4-OCH₂C₆H₄-4-Cl | CH₂F |
| 876 | CH₃ | 4-OCH₂C₆H₄-4-Cl | CHF₂ |
| 877 | CH₃ | 4-OCH₂C₆H₄-4-Cl | CH₂CF₃ |
| 878 | CH₃ | 4-OCH₂C₆H₄-4-Cl | CH₂CH=CH₂ |
| 879 | CH₃ | 4-OCH₂C₆H₄-4-Cl | CH₂CH=CHCH₃ |
| 880 | CH₃ | 4-OCH₂C₆H₄-4-Cl | CH₂CH=C(CH₃)₂ |
| 881 | CH₃ | 4-OCH₂C₆H₄-4-Cl | CH₂CH=CHCl |
| 882 | CH₃ | 4-OCH₂C₆H₄-4-Cl | CH₂CH=CCl₂ |
| 883 | CH₃ | 4-OCH₂C₆H₄-4-Cl | CH₂C(CH₃)=CH₂ |
| 884 | CH₃ | 4-OCH₂C₆H₄-4-Cl | CH₂C=CH |
| 885 | CH₃ | 4-OCH₂C₆H₄-4-Cl | CH₂Si(CH₃)₃ |
| 886 | CH₃ | 4-OCH₂C₆H₄-4-Cl | CH₂-c.propyl-2,2-Cl₂ |
| 887 | CH₃ | 4-OCH₂C₆H₄-4-Cl | CH₂CN |
| 888 | CH₃ | 4-OCH₂C₆H₄-4-Cl | CH₂COOC₂H₅ |
| 889 | CH₃ | 4-OCH₂C₆H₄-4-Cl | CH(CH₃)COOC₂H₅ |
| 890 | CH₃ | 4-OCH₂C₆H₄-4-Cl | CH₂C₆H₄-3-CF₃ |
| 891 | CH₃ | 4-OCH₂C₆H₄-4-Cl | CH₂C₆H₄-4-F |
| 892 | CH₃ | 4-OCH₂C₆H₄-4-Cl | CH₂C₆H₄-3-F |
| 893 | CH₃ | 4-OCH₂C₆H₄-4-Cl | CH₂C₆H₄-2-F |

TABLE A-continued

| Compound No. | $R_2$ | $(R_5)_n$ | $A-R_7$ |
|---|---|---|---|
| 894 | $CH_3$ | 4-$OCH_2C_6H_4$-4-Cl | $C(=O)OC_2H_5$ |
| 895 | $CH_3$ | 4-$OCH_2C_6H_4$-4-Cl | $C(=O)NHCH_3$ |
| 896 | $CH_3$ | 4-$OCH_2C_6H_4$-4-Cl | $C(=O)C(=O)OC_2H_5$ |
| 797 | $CH_3$ | 4-$OCH_2C_6H_3$-3,4-$Cl_2$ | $CH_3$ |
| 898 | $CH_3$ | 4-$OCH_2C_6H_3$-3,4-$Cl_2$ | $C_2H_5$ |
| 899 | $CH_3$ | 4-$OCH_2C_6H_3$-3,4-$Cl_2$ | n-$C_3H_7$ |
| 900 | $CH_3$ | 4-$OCH_2C_6H_3$-3,4-$Cl_2$ | i-$C_3H_7$ |
| 901 | $CH_3$ | 4-$OCH_2C_6H_3$-3,4-$Cl_2$ | n-$C_4H_9$ |
| 902 | $CH_3$ | 4-$OCH_2C_6H_3$-3,4-$Cl_2$ | n-$C_6H_{13}$ |
| 903 | $CH_3$ | 4-$OCH_2C_6H_3$-3,4-$Cl_2$ | $CH_2F$ |
| 904 | $CH_3$ | 4-$OCH_2C_6H_3$-3,4-$Cl_2$ | $CHF_2$ |
| 905 | $CH_3$ | 4-$OCH_2C_6H_3$-3,4-$Cl_2$ | $CH_2CF_3$ |
| 906 | $CH_3$ | 4-$OCH_2C_6H_3$-3,4-$Cl_2$ | $CH_2CH=CH_2$ |
| 907 | $CH_3$ | 4-$OCH_2C_6H_3$-3,4-$Cl_2$ | $CH_2CH=CHCH_3$ |
| 908 | $CH_3$ | 4-$OCH_2C_6H_3$-3,4-$Cl_2$ | $CH_2CH=C(CH_3)_2$ |
| 909 | $CH_3$ | 4-$OCH_2C_6H_3$-3,4-$Cl_2$ | $CH_2CH=CHCl$ |
| 910 | $CH_3$ | 4-$OCH_2C_6H_3$-3,4-$Cl_2$ | $CH_2CH=CCl_2$ |
| 911 | $CH_3$ | 4-$OCH_2C_6H_3$-3,4-$Cl_2$ | $CH_2C(CH_3)=CH_2$ |
| 912 | $CH_3$ | 4-$OCH_2C_6H_3$-3,4-$Cl_2$ | $CH_2C\equiv CH$ |
| 913 | $CH_3$ | 4-$OCH_2C_6H_3$-3,4-$Cl_2$ | $CH_2Si(CH_3)_3$ |
| 914 | $CH_3$ | 4-$OCH_2C_6H_3$-3,4-$Cl_2$ | $CH_2$-c.propyl-2,2-$Cl_2$ |
| 915 | $CH_3$ | 4-$OCH_2C_6H_3$-3,4-$Cl_2$ | $CH_2CN$ |
| 916 | $CH_3$ | 4-$OCH_2C_6H_3$-3,4-$Cl_2$ | $CH_2COOC_2H_5$ |
| 917 | $CH_3$ | 4-$OCH_2C_6H_3$-3,4-$Cl_2$ | $CH(CH_3)COOC_2H_5$ |
| 918 | $CH_3$ | 4-$OCH_2C_6H_3$-3,4-$Cl_2$ | $CH_2C_6H_4$-3-$CF_3$ |
| 919 | $CH_3$ | 4-$OCH_2C_6H_3$-3,4-$Cl_2$ | $CH_2C_6H_4$-4-F |
| 920 | $CH_3$ | 4-$OCH_2C_6H_3$-3,4-$Cl_2$ | $CH_2C_6H_4$-3-F |
| 921 | $CH_3$ | 4-$OCH_2C_6H_3$-3,4-$Cl_2$ | $CH_2C_6H_4$-2-F |
| 922 | $CH_3$ | 4-$OCH_2C_6H_3$-3,4-$Cl_2$ | $C(=O)OC_2H_5$ |
| 923 | $CH_3$ | 4-$OCH_2C_6H_3$-3,4-$Cl_2$ | $C(=O)NHCH_3$ |
| 924 | $CH_3$ | 4-$OCH_2C_6H_3$-3,4-$Cl_2$ | $C(=O)C(=O)OC_2H_5$ |

In Tables 2.1 and 2.2, the $^{13}$C-NMR data of the compounds 1-[4-(3-trifluoromethyl-phenylmethoxy)-phenyl]-1,2-propanedione 1-E-[methyloxime]-2-oxime and 1-[4-(3-trifluoromethylphenylmethoxy)-phenyl]-1,2-propanedione 1-Z-[methyloxime]-2-oxime (which was prepared by one of the known processes and from which the E/Z isomer mixture formed in the preparation was isolated) or, respectively, methyl 2-[[[(1-methyl-2-(4-(3-trifluoromethylphenylmethoxy)-phenyl)-2-E-[methoxyimino]ethylidene)amino]oxy]methyl]-α-(methoxymethylene)-phenylacetate (compound A225 in Table 1) are shown. The similar chemical shifts of atoms 1 and 4 of compound A in Table 2.1 and those in Table 2.2 confirm the E configuration of the compounds of the formula I.

TABLE 2.1

$^{13}$C-NMR shifts and $^1J_{cc}$ coupling constants of 1-[4-(3-trifluoromethylphenylmethoxy)-phenyl]-1,2-propanedione 1-E-[methyloxime]-2-oxime (A) and 1-[4-(3-trifluoromethylphenylmethoxy)-phenyl]-1,2-propanedione 1-Z-[methyloxime]-2-oxime (B)

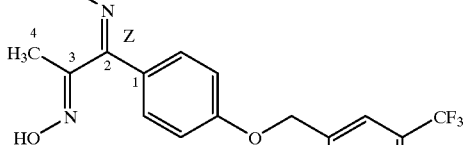

A

TABLE 2.1-continued $^{13}$C-NMR shifts and $^1J_{cc}$ coupling constants of 1-[4-(3-trifluoromethylphenylmethoxy)-phenyl]-1,2-propanedione 1-E-[methyloxime]-2-oxime (A) and 1-[4-(3-trifluoromethylphenylmethoxy)-phenyl]-1,2-propanedione 1-Z-[methyloxime]-2-oxime (B)

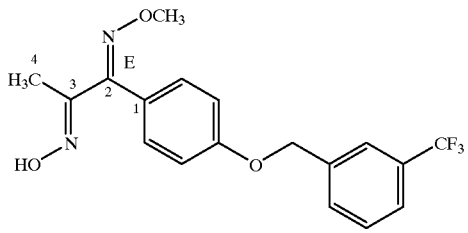

B

| Compound | Atom No. | Shift δ (ppm) | Coupling $^1J_{cc}$ (Hz) |
|---|---|---|---|
| A | 1 | 125.6 | $J_{12}$ = 56.0 |
|   | 3 | 155.0 | $J_{23}$ = 72.0 |
|   | 4 | 10.1 | $J_{34}$ = 43.0 |
| B | 1 | 127.8 | $J_{12}$ = 69.0 |
|   | 3 | 452.1 | $J_{23}$ = 56.5 |
|   | 4 | 14.4 | $J_{34}$ = 41.5 |

TABLE 2.2

$^{13}$C-NMR shifts of methyl 2-[[[(1-methyl-2-(4-(3-trifluoromethylphenylmethoxy)-phenyl)-2-E-[methoxyimino]ethylidene)amino]oxy]methyl]-α-(methoxymethylene)-phenylacetate (compound 1.225)

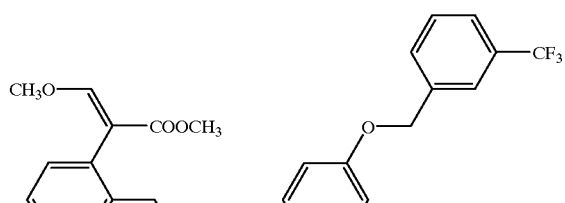

| Atom No. | Shift δ (ppm) |
|---|---|
| 1 | 124.9 |
| 2 | 155.1 |
| 3 | 155.0 |
| 4 | 11.1 |

What is claimed is:

1. A process for the preparation of a compound of the formula

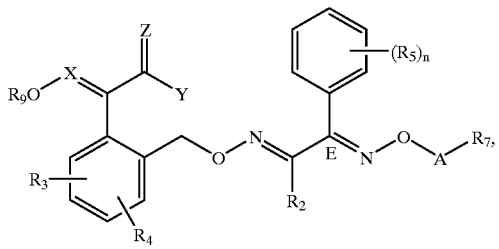

(I)

and, where appropriate, their tautomers, in each case in the free form or salt form, in which either X is CH or N, Y is $OR_1$ and Z is O, or X is N, Y is $NHR_8$ and Z is O, S or S(=O);

$R_1$ is $C_1$–$C_4$alkyl;

$R_2$ is H, $C_1$–$C_4$alkyl, halogeno-$C_1$–$C_4$alkyl, $C_3$–$C_6$cycloalkyl or $C_1$–$C_4$alkoxymethyl;

$R_3$ and $R_4$ independently of one another are H, $C_1$–$C_4$alkyl, $C_1$–$C_4$alkoxy, OH, CN, $NO_2$, a ($C_1$–$C_4$alkyl)$_3$—Si group, where the alkyl groups can be identical or different, halogen, ($C_1$–$C_4$alkyl)S(=O)$_m$, (halogeno-$C_1$–$C_4$alkyl)S(=O)$_m$, halogeno-$C_1$–$C_4$alkyl or halogeno-$C_1$–$C_4$alkoxy;

$R_5$ is $C_1$–$C_6$alkyl, halogeno-$C_1$–$C_6$alkyl, $C_1$–$C_6$alkoxy, halogeno-$C_1$–$C_6$alkoxy, $C_1$–$C_6$-alkylthio, halogen-$C_1$–$C_6$alkylthio, $C_1$–$C_6$alkylsulfinyl, halogeno-$C_1$–$C_6$alkylsulfinyl, $C_1$–$C_6$alkyl-sulfonyl, halogeno-$C_1$–$C_6$alkylsulfonyl, $C_1$–$C_6$alkoxy-$C_1$–$C_6$alkyl, halogeno-$C_1$–$C_6$alkoxy-$C_1$–$C_6$alkyl, $C_1$–$C_6$alkylthio-$C_1$–$C_6$alkyl, halogeno-$C_1$–$C_6$alkylthio-$C_1$–$C_6$alkyl, $C_1$–$C_6$alkyl-sulfinyl-$C_1$–$C_6$alkyl, halogeno-$C_1$–$C_6$-alkylsulfinyl-$C_1$–$C_6$alkyl, $C_1$–$C_6$-alkylsulfonyl-$C_1$–$C_6$alkyl, halogeno-$C_1$–$C_6$-alkylsulfonyl-$C_1$–$C_6$alkyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylaminocarbonyl, $C_1$–$C_4$-alkoxyiminomethyl; di($C_1$–$C_6$alkyl)-aminocarbonyl, where the alkyl groups can be identical or different; $C_1$–$C_6$-alkylaminothiocarbonyl; di($C_1$–$C_6$alkyl)-aminothiocarbonyl, where the alkyl groups can be identical or different; $C_1$–$C_6$-alkylamino, di($C_1$–$C_6$alkyl)-amino, where the alkyl groups can be identical or different; halogen, $NO_2$, CN, $SF_5$, thioamido, thiocyanatomethyl; an unsubstituted or mono- to tetrasubstituted $C_1$–$C_4$alkylenedioxy group, where the substituents are selected from the group consisting of $C_1$–$C_4$alkyl and halogen; or $QR_6$, where, if n is greater than 1, the radicals $R_5$ can be identical or different; $R_6$ is $C_2$–$C_6$alkenyl or $C_2$–$C_6$alkynyl, which are unsubstituted or substituted by 1 to 3 halogen atoms; ($C_1$–$C_4$alkyl)$_3$Si, where the alkyl groups can be identical or different; CN; or an unsubstituted or mono- to pentasubstituted $C_3$–$C_6$cycloalkyl, aryl or heterocyclyl group, where the substituents are selected from the group consisting of halogen, $C_1$–$C_6$alkyl, halogeno-$C_1$–$C_6$alkyl, $C_1$–$C_6$alkoxy, halogeno-$C_1$–$C_6$alkoxy, phenoxy, naphthoxy and CN;

A either is a direct bond, $C_1$–$C_{10}$alkylene, —C(=O)—,—C(=S)— or halogeno-$C_1$–$C_{10}$alkylene and $R_7$ is a radical $R_{10}$, or is $C_1$–$C_{10}$alkylene, —C(=O)—,—C(=S)— or halogeno-$C_1$–$C_{10}$alkylene and $R_7$ is $OR_{10}$, $N(R_{10})_2$, where the radicals $R_{10}$ can be identical or different, or —S(=O)$_q R_{10}$;

$R_8$ is H or $C_1$–$C_4$alkyl;

$R_9$ is methyl, fluoromethyl or difluoromethyl;

$R_{10}$ is H; an unsubstituted or substituted $C_1$–$C_6$alkyl, $C_2$–$C_6$alkenyl or $C_2$–$C_6$alkynyl group, where the substituents are selected from the group consisting of halogen; ($C_1$–$C_4$alkyl)$_3$Si, where the alkyl groups can be identical or different; $C_3$–$C_6$cyclo-alkyl, which is unsubstituted or substituted by halogen; $C_1$–$C_6$alkoxycarbonyl, which is unsubstituted or substituted by halogen; unsubstituted or substituted aryl, where the substituents are selected from the group consisting of halogen, halogeno-$C_1$–$C_4$alkyl and CN; a ($C_1$–$C_4$alkyl)$_3$Si group, where the alkyl groups can be identical or different; $C_3$–$C_6$cycloalkyl, which is unsubstituted or substituted by halogen; $C_1$–$C_6$alkoxycarbonyl which is unsubstituted or substituted by halogen; or an unsubstituted or substituted aryl or heterocyclyl group, where the substituents are selected from the group consisting of halogen and halogeno-$C_1$–$C_4$alkyl;

Q is a direct bond, $C_1$–$C_6$alkylene, $C_1$–$C_6$alkenylene, $C_2$–$C_6$alkynylene, O, O($C_1$–$C_6$alkylene), ($C_1$–$C_6$alkylene)O, S(=O)$_p$, S(=O)$_p$($C_1$–$C_6$alkylene) or ($C_1$–$C_6$alkylene)S(=O)$_p$;

m is 0, 1 or 2;

n is 0, 1, 2, 3, 4 or 5;

p is 0, 1 or 2; and q is 0, 1 or 2, and the C=N double bond marked with E has the E configuration, in which process

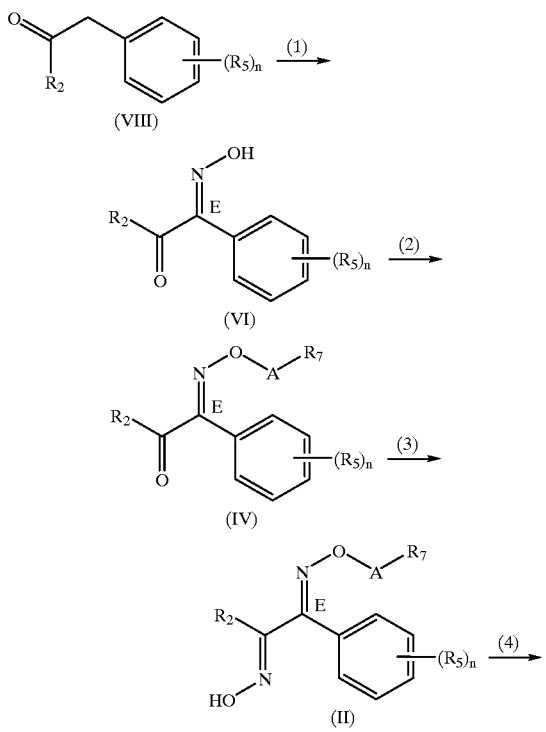

(1) a compound of formula (VIII) in which $R_2$, $R_5$ and n are as defined for formula (I), or a possible tautomer thereof, in each case in the free form or in salt form, is reacted with a $C_1$–$C_6$alkyl nitrite;

(2) the resulting E-isomer of formula (VI) is reacted with a compound of the formula (VII) $R_7$—A—$X_2$, in which A and $R_7$ are as defined for formula (I) and $X_2$ is a leaving group;

(3) reacting the resulting compound of formula (IV) in which $R_2$, $R_5$, A, $R_7$ and n are as defined for formula (I) and the C=N double bond marked with E has the E configuration, or a possible tautomer thereof, in each case in the free form or in salt form, with hydroxylamine or a salt thereof; and (4) reacting the resulting compound of formula (II) in which A, $R_2$, $R_5$, $R_7$ and n are as defined for formula (I) and the C=N double bond marked with E has the E configuration, or a possible tautomer thereof, in each case in the free form or in salt form, with a compound of the formula

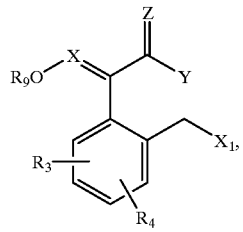

(III)

in which X, Y, Z, $R_3$, $R_4$ and $R_5$ are as defined for formula (I) and $X_1$ is a leaving group, or a tautomer thereof, in each case in the free from or in salt form, in order to obtain the compound of formula (I).

2. A process according to claim 1, wherein a compound of the formula (III) in which $X_1$ is halogen is used.

3. A process according to claim 1, wherein a compound of the formula (III) in which $X_1$ is chlorine is used.

4. A process according to claim 1, wherein the reaction of a compound of formula (II) with a compound of formula (III) is carried out in the presence of a base.

5. A process according to claim 4, wherein the reaction is carried out in the presence of a base selected from the group consisting of alkali metal and alkaline earth metal hydroxides hydrides, amides, alkanolates, acetates, carbonates, dialkylamides and alkylsilylamides.

6. A process according to claim 5, wherein the base is sodium hydride.

7. A process according to claim 1, wherein a compound of the formula (VII) in which $X_2$ is halogen is used.

8. A process according to claim 1, wherein a compound of the formula (VII) in which $X_2$ is chlorine is used.

9. A process according to claim 1, wherein the reaction of the compound of the formula (VI) with the compound of the formula (VII) is carried out in the presence of a base.

10. A process according to claim 9, wherein the reaction is carried out in the presence of a base selected from the group consisting of alkali metal and alkaline earth metal hydroxides, hydrides, amides, alkanolates, acetates, carbonates, dialkylamides and alkylsilylamides.

11. A process according to claim 1 for the preparation of a compound of the formula

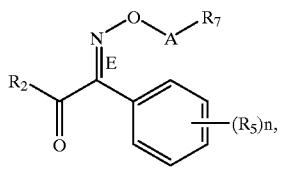

(IV)

in which A, $R_2$, $R_5$, $R_7$ and n are as defined for formula (I) and the C=N double bond marked with E has the E configuration, which comprises reacting at 0–80° C. the compound of the formula

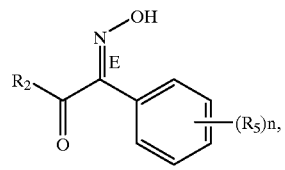

(VI)

in which $R_2$, $R_5$ and n are as defined for formula (I) and the C=N double bond marked with E has the E configuration, with a compound of the formula $R_7$—A—$X_2$ (VII), in which A and $R_7$ are as defined for formula (I) and $X_2$ is a leaving group.

12. A process according to claim 11, wherein a compound of the formula (VII) in which $X_2$ is halogen is used.

13. A process according to claim 1 for the preparation of a compound of the formula

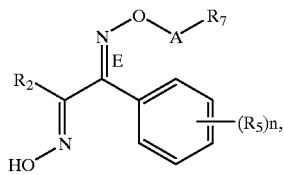

(II)

in which A, $R_2$, $R_5$, $R_7$ and n are as defined for formula (I) and the C=N double bond marked with E has the E configuration, which comprises reacting at 0–80°C. the compound of the formula

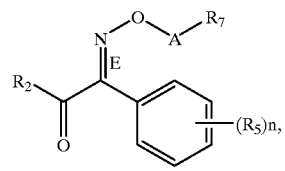

(IV)

in which A, $R_2$, $R_5$, $R_7$ and n are as defined for formula (I) and the C=N double bond marked with E has the E configuration, with hydroxylamine or a salt thereof.

14. A process according to claim 13, wherein the reaction is carried out with hydroxylamine hydrochloride.

15. A process according to claim 1 for the preparation of a compound of the formula

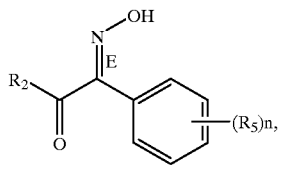

in which $R_2$, $R_5$ and n are as defined for formula (I) and the C=N double bond marked with E has the E configuration, which comprises reacting at 0–80° C. the compound of the formula

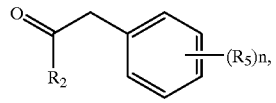

in which $R_2$, $R_5$ and n are as defined for formula (I), with a $C_1$–$C_6$alkylnitrite.

16. A process according to claim 15, wherein the reaction is carried out in the presence of a base.

17. A process according to claim 1 for the preparation of a compound of the formula (I), which comprises reacting the compound of the formula (VI), with a compound of the formula (VII), and reacting it with hydroxylamine or a salt thereof, if appropriate in the presence of a basic or acid catalyst, and further reacting the compound thus obtainable, of the formula (II), with a compound of the formula (III).

* * * * *